(12) United States Patent
Oguni et al.

(10) Patent No.: US 9,974,610 B2
(45) Date of Patent: May 22, 2018

(54) ENDOSCOPE TREATMENT SYSTEM AND TREATMENT TOOL FOR ENDOSCOPE

(71) Applicant: OLYMPUS CORPORATION, Hachioji-shi, Tokyo (JP)

(72) Inventors: Kohei Oguni, Tokyo (JP); Tsukasa Kobayashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/221,045

(22) Filed: Jul. 27, 2016

(65) Prior Publication Data
US 2016/0331452 A1 Nov. 17, 2016

Related U.S. Application Data

(63) Continuation of application No. PCT/JP2015/056072, filed on Mar. 2, 2015.

(30) Foreign Application Priority Data

Mar. 4, 2014 (JP) .................................. 2014-042053

(51) Int. Cl.
*A61B 1/00* (2006.01)
*A61B 18/14* (2006.01)
(Continued)

(52) U.S. Cl.
CPC ............ *A61B 18/1492* (2013.01); *A61B 1/00* (2013.01); *A61B 1/018* (2013.01); *A61B 18/14* (2013.01);
(Continued)

(58) Field of Classification Search
CPC .......... A61B 1/018; A61B 2018/00166; A61B 2018/1407; A61B 2018/144;
(Continued)

(56) References Cited

U.S. PATENT DOCUMENTS 5,921,971 A * 7/1999 Agro ................. A61M 25/0028
604/264
6,606,515 B1 8/2003 Windheuser et al.
(Continued)

FOREIGN PATENT DOCUMENTS

EP 1 745 737 A1 1/2007
JP H08-71081 A 3/1996
(Continued)

OTHER PUBLICATIONS

Jun. 2, 2015 International Search Report issued in International Patent Application No. PCT/JP2015/056072.
(Continued)

*Primary Examiner* — Timothy J Neal
*Assistant Examiner* — Aaron B Fairchild
(74) *Attorney, Agent, or Firm* — Oliff PLC

(57) ABSTRACT

A treatment tool for an endoscope includes a sheath which includes a proximal region, a distal region, an outer circumference surface, and an inner circumference surface; a slit portion which extends from the proximal region to the distal region in the longitudinal axis direction of the sheath and is formed to pierce through the sheath from the inner circumference surface to the outer circumference surface; an inlet portion which includes an opening that is formed at the outer circumference surface in the proximal region, the opening being formed to communicate with the slit portion, and being formed to pierce through the sheath from the inner circumference surface to the outer circumference surface in a same direction with that of the slit portion, and a locking portion which is connected to the sheath to be locked to the endoscope apparatus.

11 Claims, 21 Drawing Sheets

(51) Int. Cl.
*A61B 1/018* (2006.01)
*A61B 18/00* (2006.01)
*A61M 25/01* (2006.01)
*A61M 25/06* (2006.01)

(52) U.S. Cl.
CPC .......... *A61B 2018/00166* (2013.01); *A61B 2018/00601* (2013.01); *A61B 2018/144* (2013.01); *A61B 2018/1407* (2013.01); *A61M 2025/0188* (2013.01); *A61M 2025/0681* (2013.01)

(58) Field of Classification Search
CPC .. A61M 2025/0034; A61M 2025/0681; A61M 25/0668; A61M 2025/0188
See application file for complete search history.

(56) References Cited

U.S. PATENT DOCUMENTS

| | | | |
|---|---|---|---|
| 2004/0015050 A1 | 1/2004 | Goto et al. | |
| 2005/0065399 A1* | 3/2005 | Sasaki | A61B 1/00137 600/106 |
| 2006/0247494 A1 | 11/2006 | Nakagawa et al. | |
| 2008/0033238 A1 | 2/2008 | Takahashi | |
| 2009/0221870 A1 | 9/2009 | Nakagawa et al. | |
| 2011/0196344 A1 | 8/2011 | Agro et al. | |

FOREIGN PATENT DOCUMENTS

| | | |
|---|---|---|
| JP | 2000-237202 A | 9/2000 |
| JP | 2001-070316 A | 3/2001 |
| JP | 2001-511023 A | 8/2001 |
| JP | 2002-514099 A | 5/2002 |
| JP | 2004-049891 A | 2/2004 |
| JP | 2005-349186 A | 12/2005 |
| JP | 2006-204476 A | 8/2006 |
| JP | 2007-325721 A | 12/2007 |
| JP | 2008-509726 A | 4/2008 |
| WO | 98/10820 A1 | 3/1998 |
| WO | 98/10821 A1 | 3/1998 |
| WO | 2006/020374 A2 | 2/2006 |
| WO | 2014/010335 | 1/2014 |

OTHER PUBLICATIONS

Oct. 23, 2017 Extended European Search Report issued in European Patent Application No. 15759296.5.

* cited by examiner

ENDOSCOPE TREATMENT SYSTEM AND TREATMENT TOOL FOR ENDOSCOPE

This application is a continuation application based on a PCT International Application No. PCT/JP2015/056072, filed on Mar. 2, 2015, whose priority is claimed on Japanese Patent Application No. 2014-042053, filed on Mar. 4, 2014. The contents of both the PCT International Application and the Japanese Patent Application are incorporated herein by reference.

BACKGROUND OF THE INVENTION

Field of the Invention

The present invention relates to an endoscope treatment system and a treatment tool for an endoscope.

Description of Related Art

As a procedure for incising the sphincter of a duodenal papilla portion while observing a duodenal papilla using an endoscope apparatus, endoscopic sphincterotomy (EST) is known. For example, a treatment tool which is used in the EST is disclosed in U.S. Pat. No. 6,606,515, Japanese Unexamined Patent Application, First Publication No. 2001-070316, Japanese Unexamined Patent Application, First Publication No. 2000-237202, and Published Japanese Translation No. 2001-511023 of the PCT International Publication. U.S. Pat. No. 6,606,515 discloses a guide wire insertion tool in which a funnel-shaped extension portion is provided, the extension portion of which communicates with a lumen of a catheter in order to easily insert a guide wire into the lumen of the catheter. Japanese Unexamined Patent Application, First Publication No. 2001-070316 discloses a high-frequency knife in which a guide arm portion is formed on a knife wire, and an incision portion of the knife wire can be directed to a desired direction by disposing the guide arm portion in a slit which is formed in a sheath. Japanese Unexamined Patent Application, First Publication No. 2000-237202 discloses a treatment tool which can safely perform the EST by providing an incision portion which is not insulated, and an insulation portion which is insulated in a portion except for the incision portion, on a distal end portion of a high-frequency knife wire. Published Japanese Translation No. 2001-511023 of the PCT International Publication discloses a bile duct treatment catheter which includes a groove which communicates with a guide wire lumen from a position outside a catheter shaft and extends in a longitudinal direction of the shaft so as to easily replace a guide wire.

SUMMARY OF THE INVENTION

According to a first aspect of the present invention, a treatment tool for an endoscope which is inserted into a treatment tool channel of an endoscope apparatus which includes a tubular member that is capable of being operated to be bent and a bending operation section that is provided to bend the tubular member, includes a sheath which includes a proximal region, a distal region, an outer circumference surface, and an inner circumference surface, the inner circumference surface being formed to define a lumen which is extended along a longitudinal axis of the sheath and through which a guide wire is inserted; a slit portion which extends from the proximal region to the distal region in the longitudinal axis direction of the sheath and is formed to pierce through the sheath from the inner circumference surface to the outer circumference surface; an inlet portion which includes an opening that is formed at the outer circumference surface in the proximal region of the sheath, the opening being formed to communicate with the slit portion, and being formed to pierce through the sheath from the inner circumference surface to the outer circumference surface in a same direction with that of the slit portion, and a locking portion which is connected to the sheath, and is capable of being locked to the endoscope apparatus, in a state in which an opening direction of the inlet portion of the sheath faces the bending operation section.

According to a second aspect of the present invention, the treatment tool for an endoscope according to the first aspect may include an insertion portion which includes the sheath and is capable of being inserted into a body; and an operation portion which is disposed at a proximal end of the insertion portion, The operation portion may include a port where a through-hole is formed, the through-hole being formed to communicate with the inlet portion and capable of being inserted through by the guide wire, and the through-hole of the port may be open to a direction intersecting a center axis of the lumen.

According to a third aspect of the present invention, in the treatment tool for an endoscope according to the second aspect, the locking portion may include a hook which has elasticity, the hook being formed in a C-shape so as to surround a portion of an outer circumferential surface of the holding portion of the endoscope apparatus, and a center axis of the through-hole of the port and a center axis of a circumference on an inner circumferential surface surrounding the holding portion in the hook may be parallel with each other.

According to a fourth aspect of the present invention, in the treatment tool for an endoscope according to the first aspect, an operation portion of the treatment tool for an endoscope may include a tubular portion which includes an inner space into which the proximal region of the sheath is capable of being inserted and includes a communication port communicated with the inner space; a port-fixing portion which is provided to fix the proximal region of the sheath to the tubular portion such that a direction of the opening of the inlet portion coincides with a direction of the communication port of the tubular portion, in a state in which the sheath is inserted into the treatment tool channel and the locking portion is locked to the endoscope apparatus; and a notch portion which includes a gap formed to communicate with the slit portion from a distal end of the communication port of the tubular portion to a distal end of the tubular portion along a longitudinal axis of the slit portion, in a state in which the sheath is inserted into the treatment tool channel and the locking portion is locked to the endoscope apparatus.

According to a fifth aspect of the present invention, the treatment tool for an endoscope according to the fourth aspect may further include a knife wire which is disposed on the distal region of the sheath and provided to incise the tissues. The notch portion may have a C-shape in a cross section perpendicular to the longitudinal axis of the sheath.

According to a sixth aspect of the present invention, the treatment tool for an endoscope according to the first aspect may include an insertion portion which includes the sheath and is capable of being inserted into a body; and an operation portion which is disposed at a proximal end of the insertion portion. The insertion portion may include a knife wire which is disposed at the sheath and incises the tissues, a second lumen which is formed in the sheath, and includes a space through which liquid is capable of flowing, an injection port at the distal region of the sheath, and a connection port at the proximal region of the sheath, and a third lumen which is formed in the sheath, into which the knife wire is inserted, and which includes a horizontal hole portion, through which the knife wire is exposed, on the distal end portion of the sheath, and an opening on the proximal end portion of the sheath. The operation portion may include a first port which communicates with the inlet portion, and at which a through-hole, into which the guide wire can be inserted, is formed, a second port which communicates with the second lumen, and a handle portion at which a slider portion for interlocking with the knife wire is formed. The first port may be a long hole which has a major axis in the center axis direction of the lumen, and the slider portion may include a finger-hooking portion which protrudes in a direction of a plane orthogonal to the center axis of the through-hole of the first port.

According to a seventh aspect of the present invention, the treatment tool for an endoscope according to the third aspect may include an insertion portion which includes the sheath and is capable of being inserted into a body; and an operation portion which is disposed at a proximal end of the insertion portion. The sheath may include a slit portion which extends in the center axis direction of the sheath and allows the inside of the lumen and the outside of the sheath to communicate with each other, and the port may include a C-shaped notch portion at a distal end of the port, the notch portion including a gap formed along the slit portion to contact with the outer circumferential surface of the sheath. The operation portion may include a connection portion in which the port is formed and which is connected to the proximal end of the sheath, an extension portion which is connected to the hook, and a main body portion which is connected to both of the connection portion and the extension portion such that the hook and the notch portion are spaced from each other.

According to an eighth aspect of the present invention, in the treatment tool for an endoscope according to the sixth aspect, the operation portion may include a shaft portion which has a center axis in a direction inclined to the longitudinal axis of the sheath and is connected to the slider portion such that the slider portion moves forward and backward in the direction of the center axis.

According to a ninth aspect of the present invention, in the treatment tool for an endoscope according to the second aspect, the slit portion may be formed between the inlet portion and the outlet portion, and may be formed such that an opening width in the circumferential direction of the sheath is smaller than the inner diameter of the lumen. The sheath may be fixed to the operation portion such that the opening edge portion approximately coincides with the inner opening edge portion or is positioned inside the inner opening edge portion, when an opening edge portion of the inlet portion and an inner opening edge portion forming a contour on the inner circumferential side of the port are projected in an extension direction of a straight line which connects the center axis of the lumen and the center axis of the sheath.

DETAILED DESCRIPTION OF THE INVENTION

Figure 1:
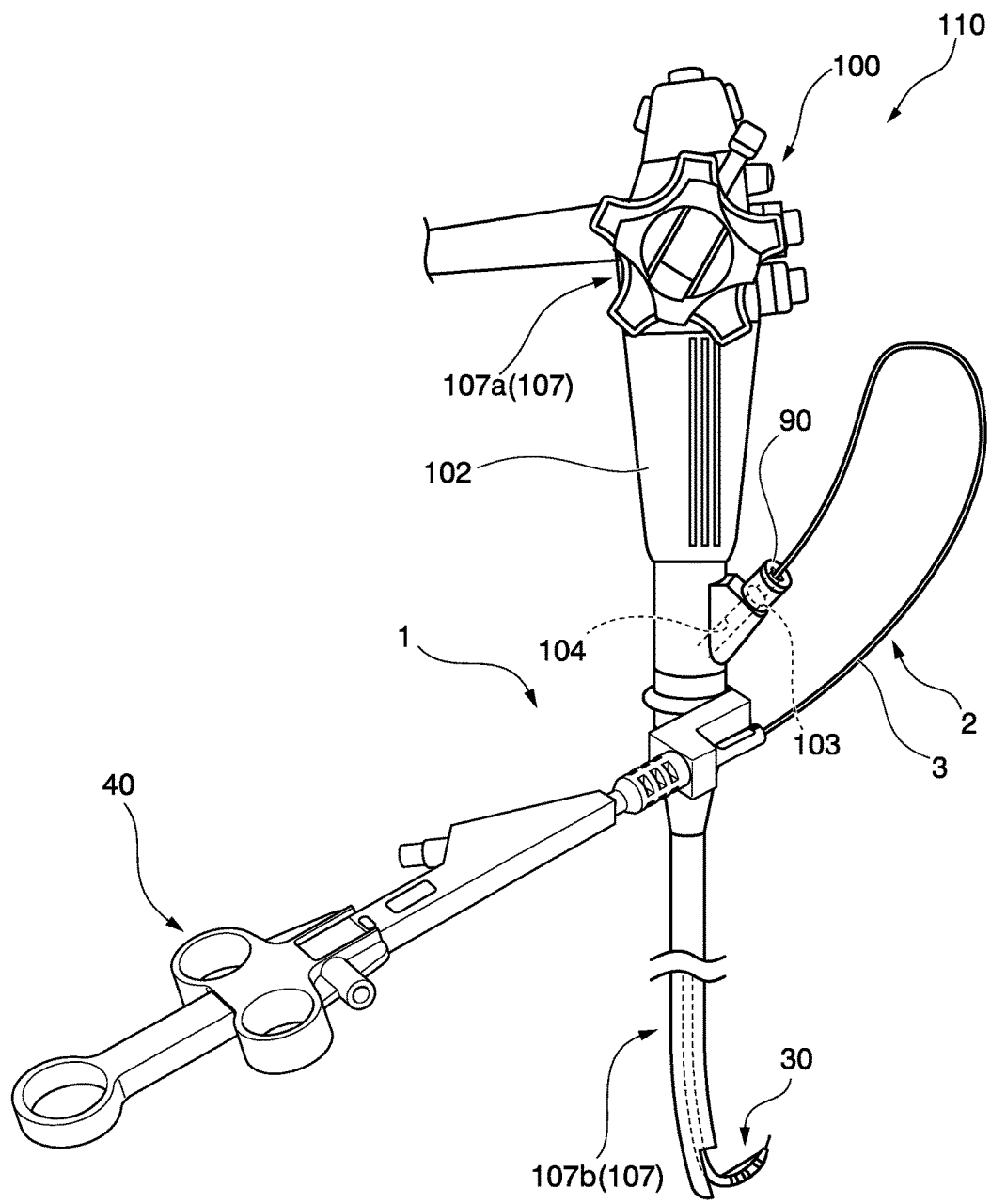
FIG. 1 is an overall view of an incision system including a treatment tool for an endoscope according to a first embodiment of the present invention.

A first embodiment of the present invention will be described. FIG. 1 is an overall view of an incision system 110 which includes a treatment tool 1 for an endoscope according to the present embodiment.

As shown in FIG. 1, the treatment tool 1 for an endoscope according to the present embodiment is a medical instrument which is used along with an endoscope apparatus 100 in order to incise a tissue in the body. The treatment tool 1 for an endoscope configures an incision system 110 (endoscope treatment system) in a state of being combined with the endoscope apparatus 100.

Figure 2:
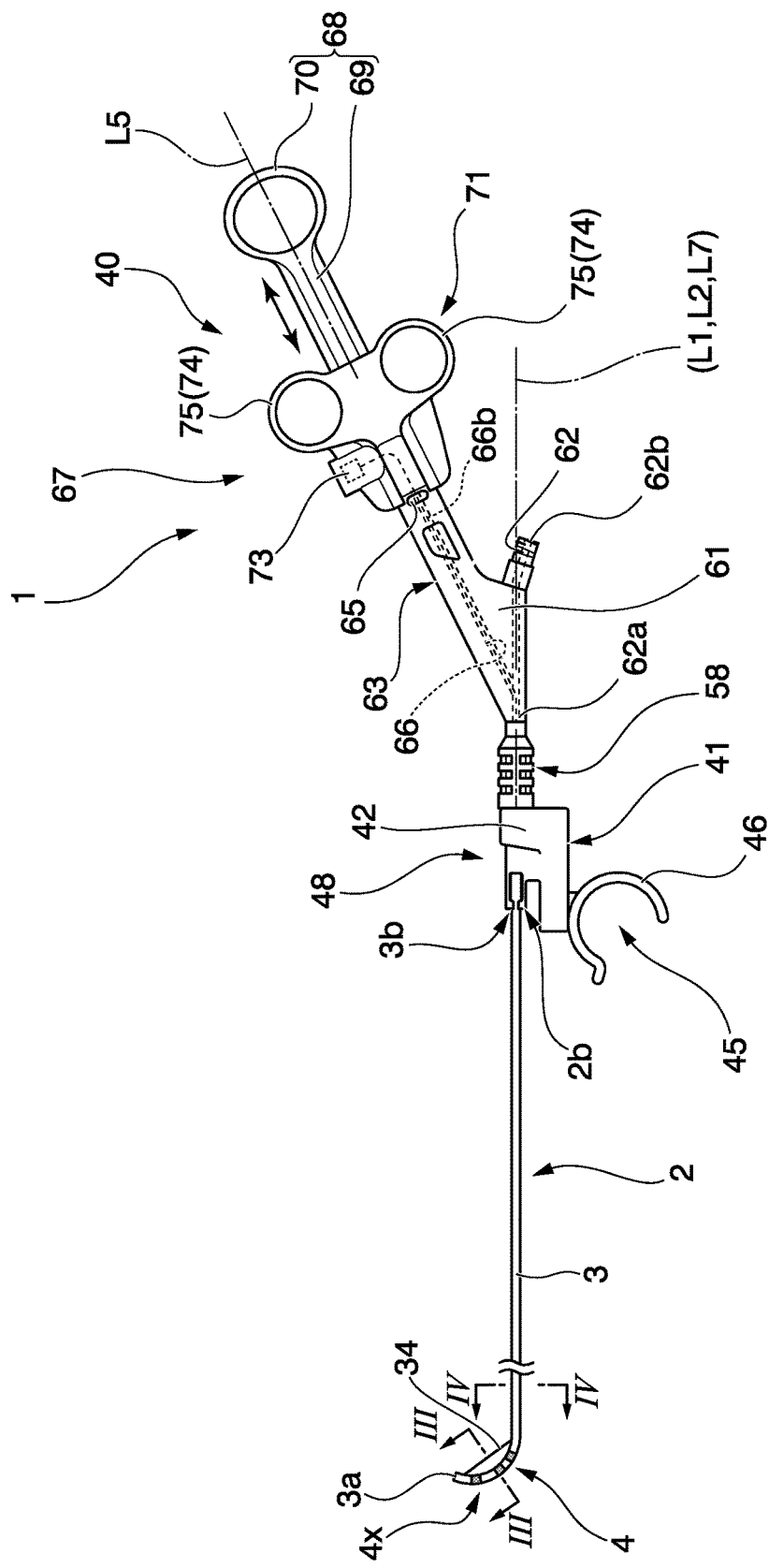
FIG. 2 is a plan view of the treatment tool for an endoscope according to the first embodiment of the present invention.
Figure 3A:
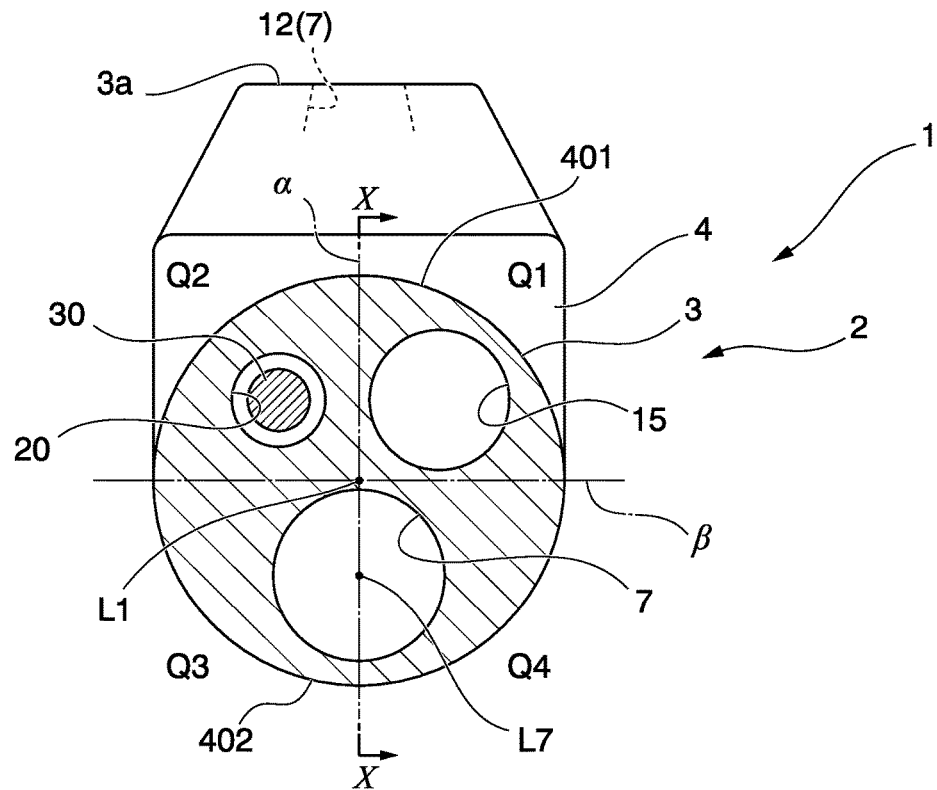
FIG. 3A is a sectional view taken along line III-III of FIG. 2.
Figure 3B:
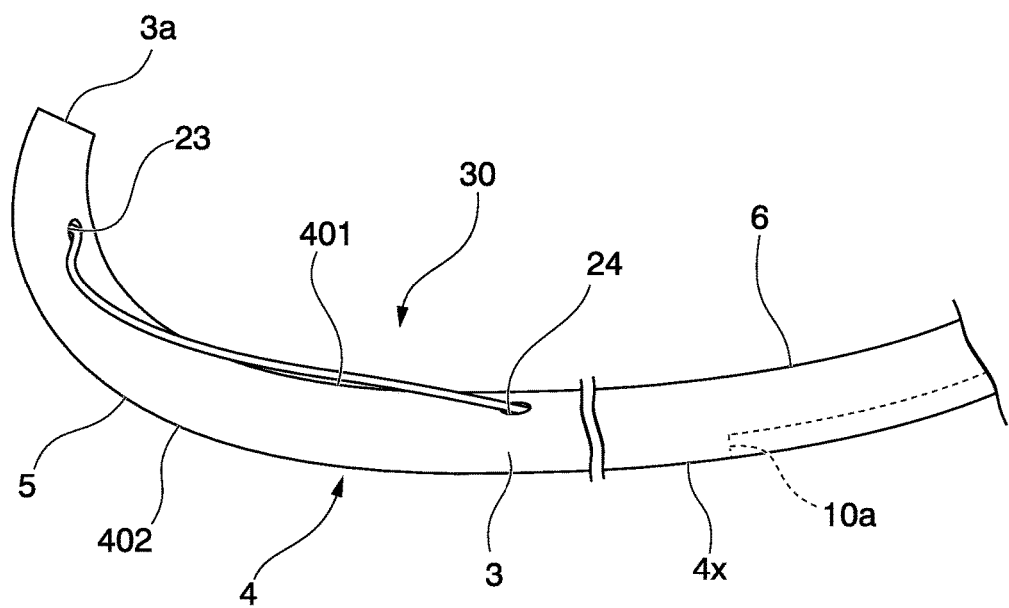
FIG. 3B is a plan view showing a distal end portion of a sheath of the treatment tool for an endoscope according to the first embodiment of the present invention.
Figure 4:
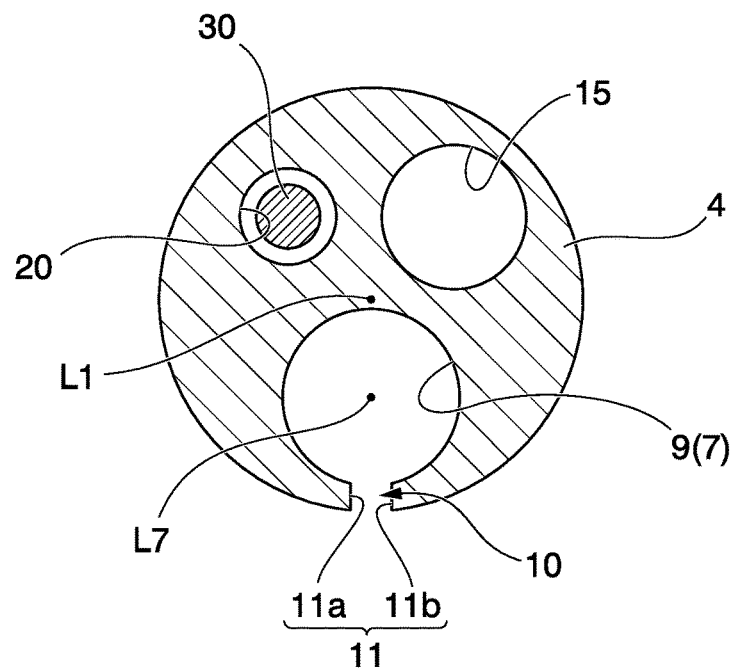
FIG. 4 is a sectional view taken along line IV-IV of FIG. 2.
Figure 5:
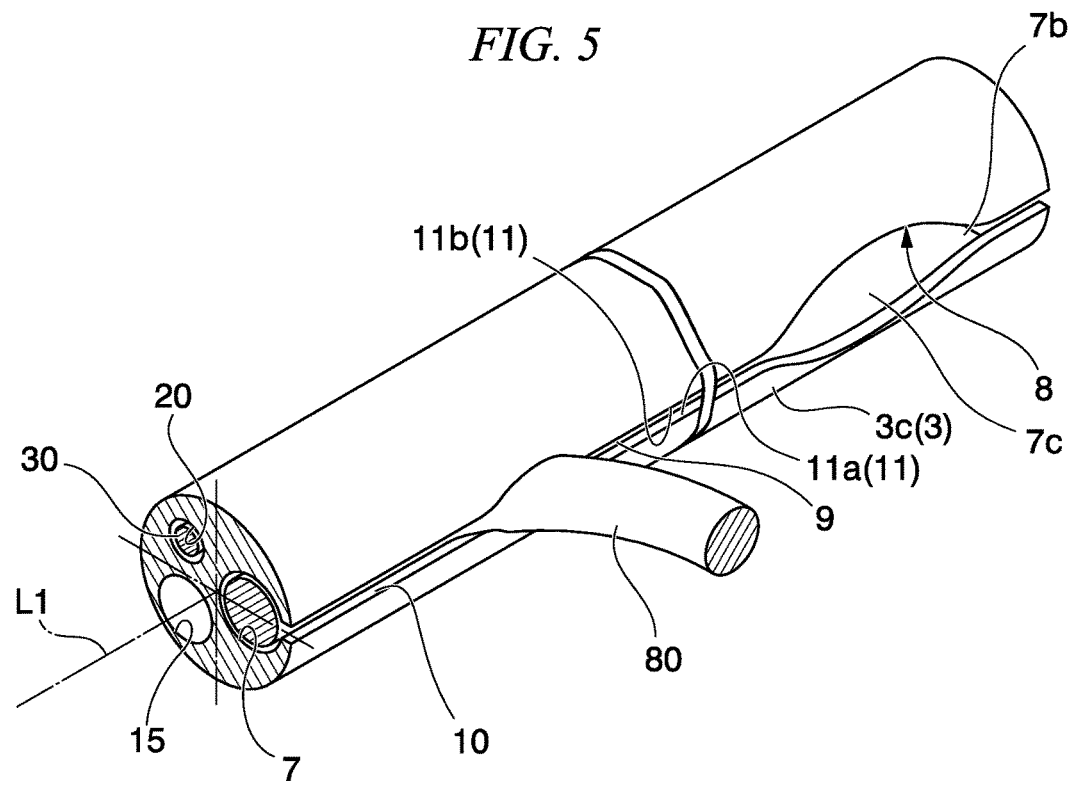
FIG. 5 is a perspective view showing a portion of the sheath in the treatment tool for an endoscope according to the first embodiment of the present invention.
Figure 6:
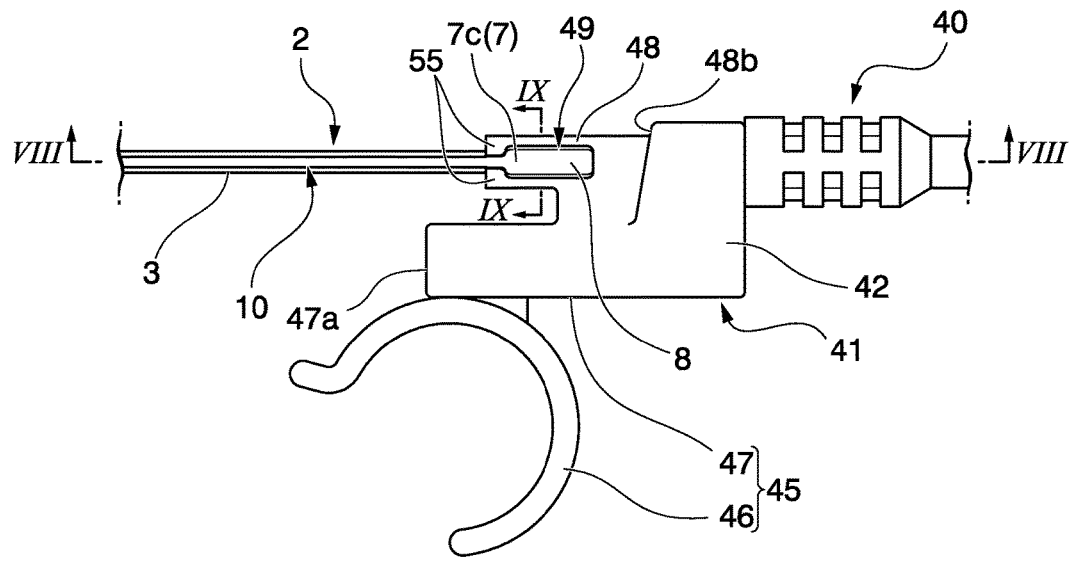
FIG. 6 is a plan view showing a portion of an operation portion of the treatment tool for an endoscope according to the first embodiment of the present invention.
Figure 7:
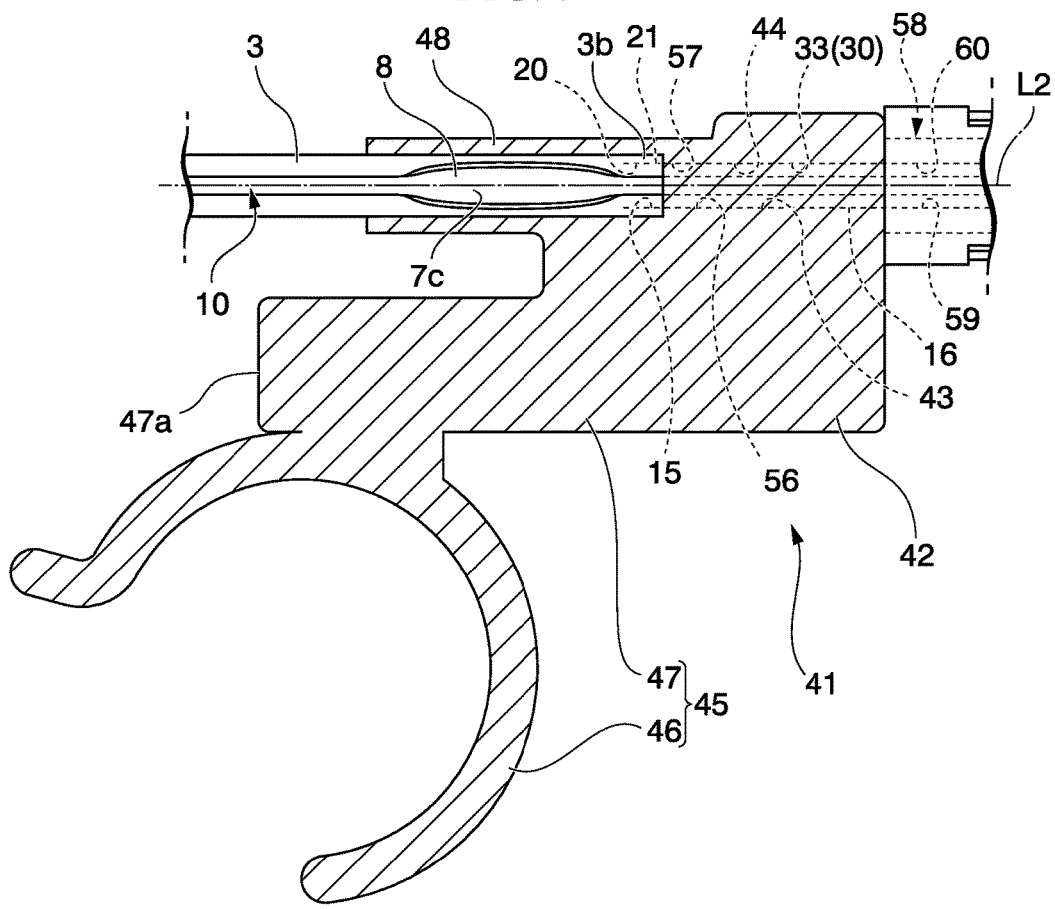
FIG. 7 is a partial sectional view showing the sheath and a distal configuration portion of the operation portion in the treatment tool for an endoscope according to the first embodiment of the present invention.
Figure 8:
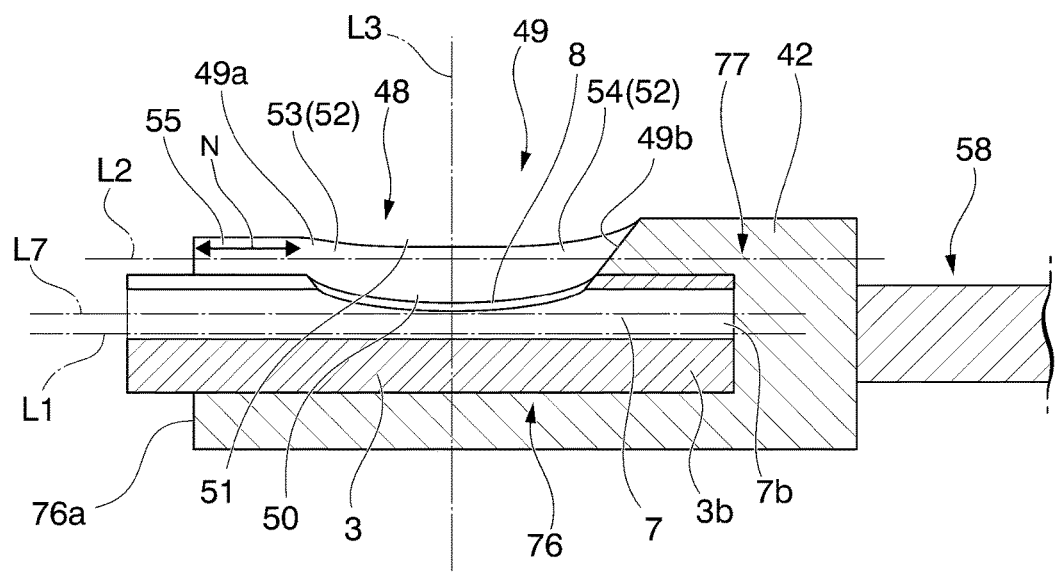
FIG. 8 is a partial sectional view showing a first port portion of the treatment tool for an endoscope according to the first embodiment of the present invention, and is a view when viewed from a direction of line VIII-VIII shown in FIG. 6.
Figure 9A:
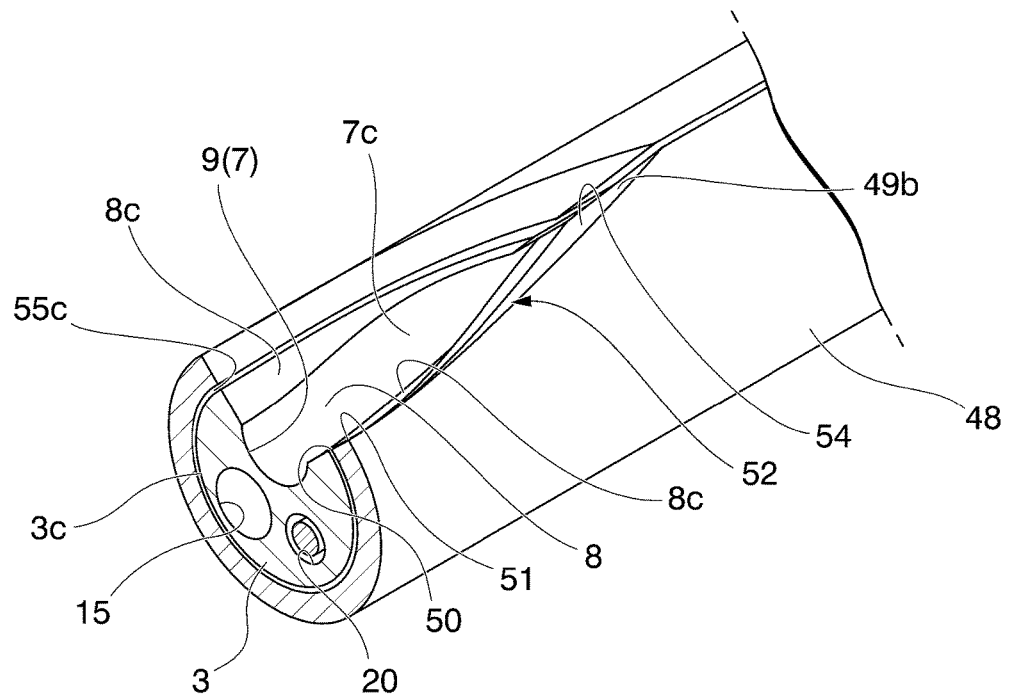
FIG. 9A is a sectional view taken along line IX-IX of FIG. 6.
Figure 9B:
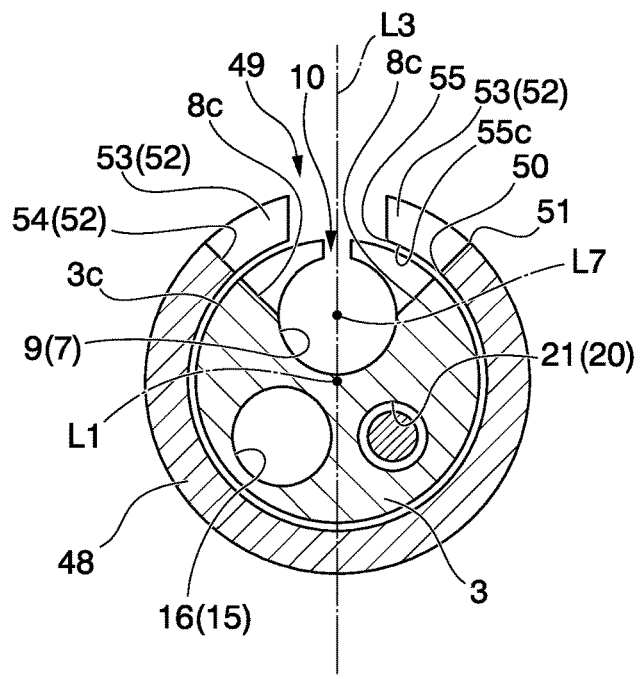
FIG. 9B is a perspective view showing the first port portion of the treatment tool for an endoscope according to the first embodiment of the present invention.
Figure 10:
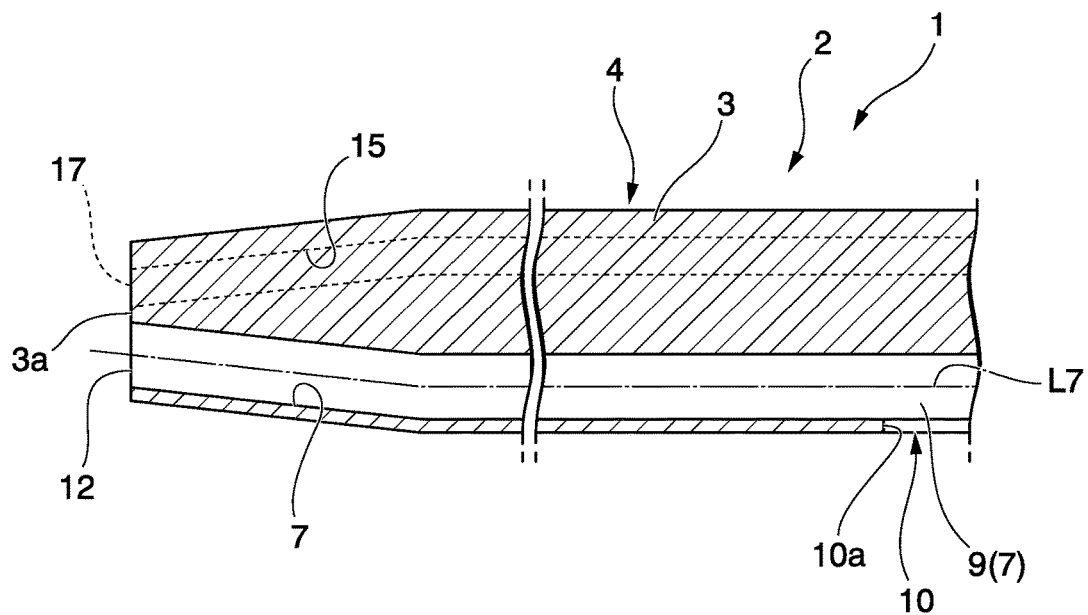
FIG. 10 is a sectional view showing the distal end portion of the sheath of the treatment tool for an endoscope according to the first embodiment of the present invention on a first virtual plane.
Figure 11:
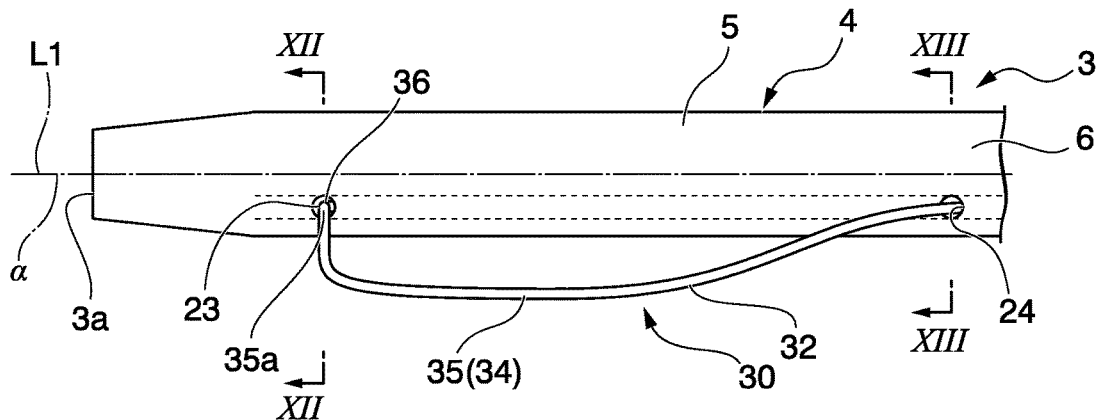
FIG. 11 is a view when the distal portion of the sheath of the treatment tool for an endoscope according to the first embodiment of the present invention is viewed from a direction perpendicular to a second virtual plane.
Figure 12:
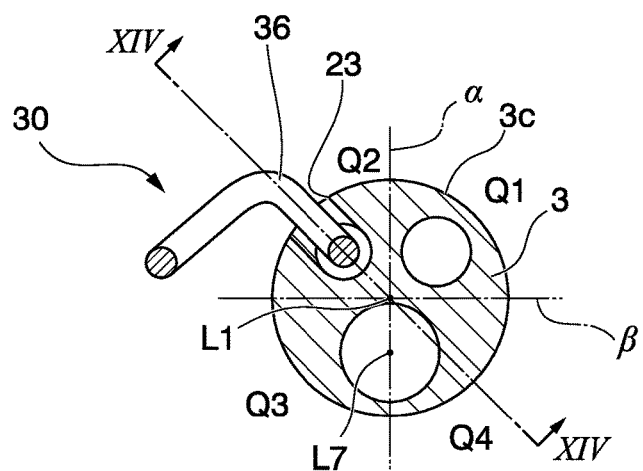
FIG. 12 is a sectional view taken along line XII-XII of FIG. 11.
Figure 13:
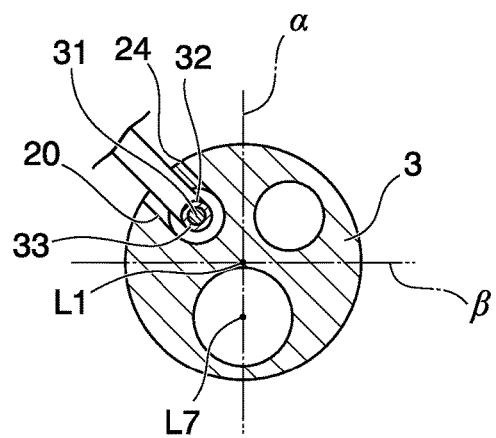
FIG. 13 is a sectional view taken along line XIII-XIII of FIG. 11.
Figure 14:
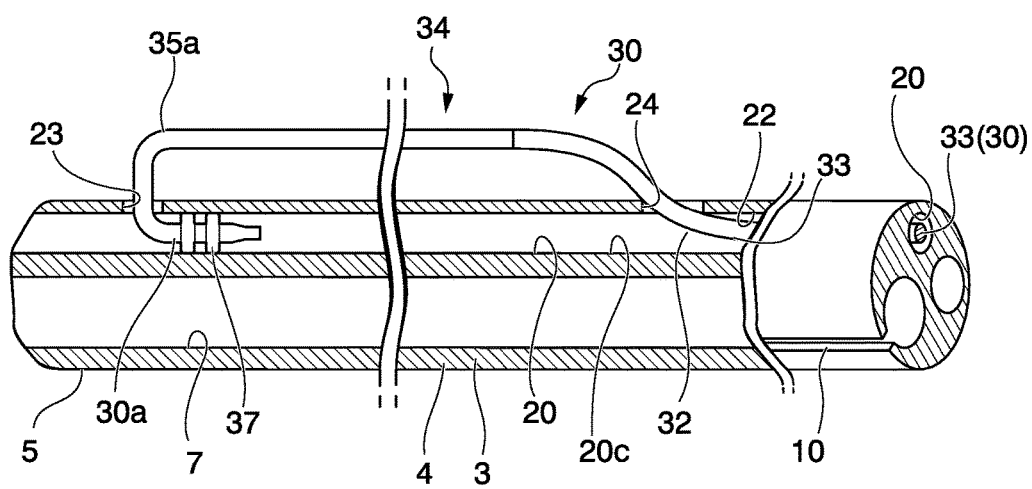
FIG. 14 is a view showing the distal portion of the sheath of the treatment tool for an endoscope according to the first embodiment of the present invention, and is a view which includes a partial sectional view of the sheath when viewed from line XIV-XIV shown in FIG. 12.

FIG. 2 is a plan view of the treatment tool 1 for an endoscope. FIG. 3A is a sectional view taken along line III-III of FIG. 2. FIG. 3B is a plan view showing a distal end portion of a sheath 3 of the treatment tool 1 for an endoscope according to the first embodiment of the present invention. FIG. 4 is a sectional view taken along line IV-IV of FIG. 2. FIG. 5 is a perspective view showing a portion of the sheath 3 in the treatment tool 1 for an endoscope. FIG. 6 is a plan view showing a portion of an operation portion 40 of the treatment tool 1 for an endoscope. FIG. 7 is a view showing the sheath 3 and a distal configuration portion 41 of the operation portion 40 in the treatment tool 1 for an endoscope, and in which only the distal configuration portion 41 of the operation portion 40 is shown in a cross section. FIG. 8 is a partial sectional view showing a first port (communication port) 49 portion of the treatment tool 1 for an endoscope, and is a view when viewed from a direction of line VIII-VIII shown in FIG. 6. FIG. 9A is a sectional view taken along line IX-IX of FIG. 6. FIG. 9B is a perspective view showing the first port 49 portion of the treatment tool 1 for an endoscope. FIG. 10 is a sectional view showing the distal end portion of the sheath 3 on a first virtual plane α. FIG. 11 is a view when the distal portion of the sheath 3 is viewed from a direction perpendicular to a second virtual plane β. FIG. 12 is a sectional view taken along line XII-XII of FIG. 11. FIG. 13 is a sectional view taken along line XIII-XIII of FIG. 11. FIG. 14 is a view showing the distal portion of the sheath 3, and includes a partial sectional view of the sheath 3 when viewed from line XIV-XIV shown in FIG. 12.

The treatment tool 1 for an endoscope includes an insertion portion 2 and an operation portion 40. The insertion portion 2 is an elongated member which is inserted into a treatment tool channel 104 of the endoscope apparatus 100. The insertion portion 2 includes the sheath 3 and a knife wire 30. As shown in FIGS. 1 and 2, the sheath 3 is an elongated member which has flexibility. In the present embodiment, the sheath 3 is formed of a resin.

Hereinafter, the operation portion 40 side of the treatment tool 1 for an endoscope is referred to as a proximal side, and a side on which the insertion portion 2 is provided and which is inserted into the body is referred to as a distal side.

Figure 35:
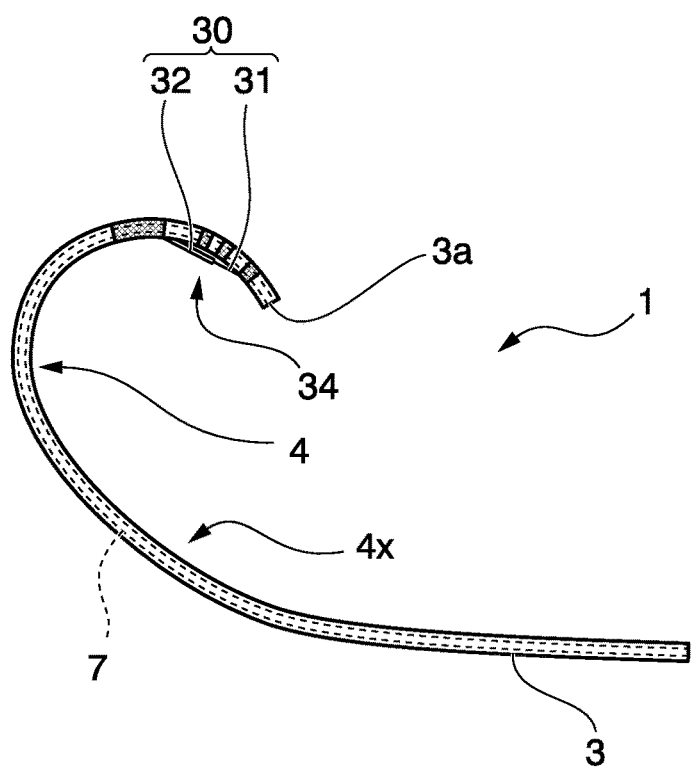
FIG. 35 is a schematic view showing a configuration of a second modification example of the first embodiment of the present invention.

As shown in FIGS. 3B and 35, the sheath 3 has a pre-curved portion 4 in a predetermined region including a distal end 3a of the sheath 3. A bending habit is applied to the pre-curved portion 4 so as to be curved in a shape which is curved in a predetermined direction, and the pre-curved portion 4 has a restoring force which restores the pre-curved portion 4 so as to be a predetermined curved shape. As shown in FIGS. 3A and 3B, the center axis L1 of the sheath 3 exists in one predetermined plane (hereinafter, referred to as a "first virtual plane α") in the pre-curved portion 4.

A distal end portion of the pre-curved portion 4 is inserted into a duodenal papilla PV (refer to FIG. 23) of a patient who is an object to be treated. As shown in FIG. 3B, a first distal communication hole 23 and a second distal communication hole 24 described below are provided in the distal end portion of the pre-curved portion 4.

As shown in FIG. 3A, the configuration of the sheath 3 is described using an orthogonal coordinate system (hereinafter, referred to as a "virtual coordinate system") in which the center axis L1 is an origin, the first virtual plane α is a vertical axis, and a plane (hereinafter, referred to as a "second virtual plane β") orthogonal to the first virtual plane α on the center axis L1 of the sheath 3 is a horizontal axis when a cross section orthogonal to the center axis L1 of the sheath 3 is viewed along the center axis L1 of the sheath 3 from the proximal end 3b (refer to FIG. 2) of the sheath 3 toward the distal end 3a. In the vertical axis of the virtual coordinate system, the bending direction of the pre-curved portion 4 is referred to as an upper side.

As shown in FIGS. 3A and 5, a first lumen 7, a second lumen 15, and a third lumen 20 are formed inside the sheath 3. The first lumen 7, the second lumen 15, and the third lumen 20 are formed to extend so as to be parallel with one another in a longitudinal direction of the sheath 3.

The first lumen 7 is a passage portion which has an inner diameter through which a guide wire 80 can move forward and backward. That is, the first lumen 7 is a lumen in which the guide wire 80 is held. A center axis L7 of the first lumen 7 is positioned on the first virtual plane α, and the first lumen 7 is positioned below the center axis L1 of the sheath 3, that is, is positioned on a third quadrant Q3 and a fourth quadrant Q4 of the virtual coordinate system. Specifically, the first virtual plane α crosses the internal space of the first lumen 7. In addition, the predetermined first virtual plane α includes the center axis L7 of the first lumen 7.

As shown in FIGS. 3A and 5, the first lumen 7 includes an outlet portion 12 which is open to the distal end 3a, a guide wire accommodation portion 9, a slit portion 10, and an inlet portion 8 which is open to the proximal end side.

Figure 34:
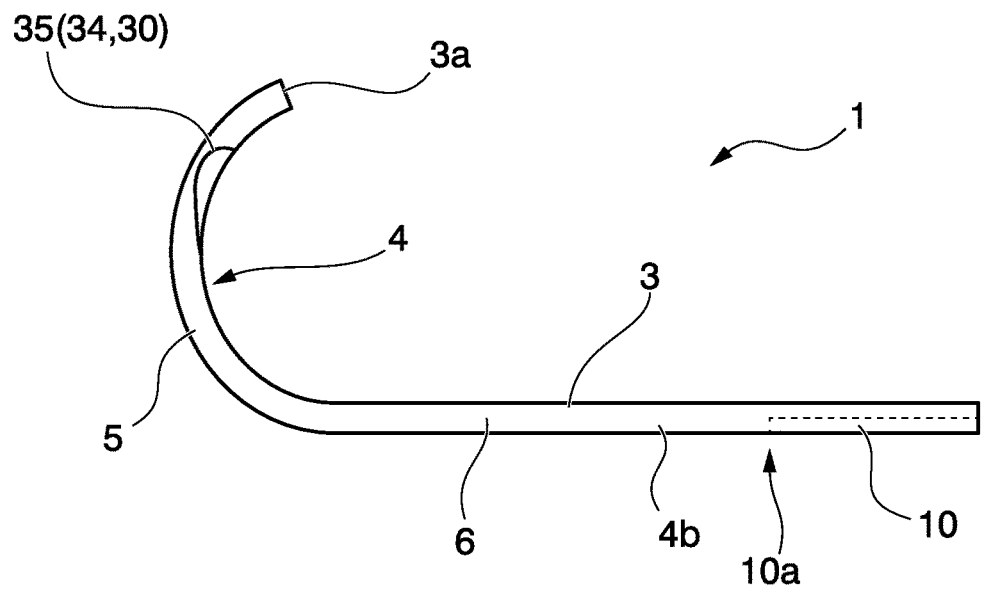
FIG. 34 is a schematic view showing a configuration of a modification example of the first embodiment of the present invention.

As shown in FIGS. 4 and 5, the slit portion 10 is an elongated notch which is open to the outer circumferential surface 3c of the sheath 3 such that the first lumen 7 communicates with the outside of the sheath 3, and which is formed so as to extend in the center axis L1 direction of the sheath 3. The slit portion 10 has a shape in which a resin member configuring the sheath 3 is cut out in the center axis L1 direction of the sheath 3. The slit portion 10 is formed along the center axis L1 of the sheath 3 at a position at which the outer circumferential surface of the pre-curved portion 4 and the predetermined first virtual plane α intersect each other in the proximal portion of the pre-curved portion 4 in the proximal region of a proximal end 4b (refer to FIG. 34) of the pre-curved portion 4. Specifically, a distal end 10a of the slit portion 10 is positioned at a portion closer to the base end side relative to the second distal communication hole 24, and is positioned at a position closer to the tip side relative to the proximal end 4b (refer to FIG. 34) of the pre-curved portion 4. The slit portion 10 extends to the inlet portion 8.

The slit portion 10 has a pair of flap portions 11 (first flap 11a and second flap 11b) which are disposed so as to be separated from each other such that an opening width of the slit portion 10 is smaller than the diameter of the guide wire 80. The flap portions 11 are a pair of elastic portions which covers the guide wire accommodation portion 9 by a resin member configuring the sheath 3. The flap portions 11 are deformed until a gap is generated which has a size by which the guide wire 80 can pass through by force of an operator when the guide wire 80 is detached from the guide wire accommodation portion 9 through the slit portion 10.

As shown in FIG. 5, the inlet portion 8 is a portion which is open to the outer circumferential surface 3c of the sheath 3 so as to have the same size as the diameter of the guide wire 80 or to have a larger size than the diameter of the guide wire 80 in the vicinity of a proximal end 7b of the first lumen 7. In other words, the inlet portion 8 is an opening portion in which an inner surface 7c of the first lumen 7 is exposed to the outside in a state where the flap portions 11 are not provided, and which has a wider width than that of the slit portion 10. That is, the inlet portion 8 has a larger width than the opening width of the slit portion 10, communicates with the first lumen 7, and is open to the outer circumferential surface 3c of the proximal portion of the sheath 3.

The length of the inlet portion 8 in the center axis L1 direction of the sheath 3 is larger than the inner diameter of the guide wire accommodation portion 9 in the first lumen 7. That is, the inlet portion 8 has a long hole shape which is long in the center axis L1 direction of the sheath 3. In addition, the shape of the inlet portion 8 may have a rectangular shape. If the shape of the inlet portion 8 has a rectangular shape, the inlet portion 8 is easily processed. Right and left ends 8c (both ends in the circumferential direction) of the inlet portion 8 in the circumferential direction of the sheath 3 may have a taper shape (refer to FIG. 9B) such that an opening area of the inlet portion 8 gradually increases from the guide wire accommodation portion 9 toward the outer circumferential surface 3c of the sheath 3.

As shown in FIG. 4, the guide wire accommodation portion 9 has a circular contour except for a boundary between the guide wire accommodation portion 9 and the slit portion 10 described below in the cross section orthogonal to the center axis L1 of the sheath 3. That is, the guide wire accommodation portion 9 has an approximately C-shaped contour shape in the cross section orthogonal to the center axis L1 of the sheath 3. The guide wire accommodation portion 9 is set to have clearance in a state where the guide wire 80 is inserted into the guide wire accommodation portion 9 such that the guide wire 80 can move forward and backward, and the inner diameter of the guide wire accommodation portion 9 is larger than the diameter of the guide wire 80 by the dimensions of the clearance. The guide wire accommodation portion 9 has an approximately C-shaped contour shape in the cross section orthogonal to the center axis L1 of the sheath 3. Specifically, the slit portion 10 is formed such that the opening width of the slit portion 10 in the circumferential direction of the sheath 3 is smaller than the inner diameter of the first lumen 7.

As shown in FIGS. 3A, 3B, and 5, the first lumen 7 has a continuous circumferential contour when viewed from a cross section orthogonal to the center axis L1 of the sheath 3 between the distal end 10a of the slit portion 10 and the distal end 3a of the sheath 3, and can hold the guide wire 80 such that the guide wire 80 can protrude from the distal end 3a of the sheath 3. The outlet portion 12 is open to the distal end 3a of the sheath 3. The outlet portion 12 communicates with the guide wire accommodation portion 9.

For example, the second lumen 15 shown in FIG. 3A may be used as a liquid-feeding lumen for feeding liquid such as a contrast agent from the proximal end 3b (refer to FIG. 2) of the sheath 3 to the distal end 3a (FIGS. 2 and 3A) of the sheath 3. In addition, the second lumen 15 can be used as a liquid-discharging lumen for removing liquid in the body.

The second lumen 15 in the pre-curved portion 4 is positioned at a first quadrant Q1 in the virtual coordinate system.

The second lumen 15 includes a proximal connection port 16 (refer to FIG. 9A) and a distal discharge port 17 (refer to FIG. 10), and can be used as a channel through which liquid flows from the proximal connection port 16 to the distal discharge port 17.

The proximal connection port 16 is an opening which communicates with a communication path 56 (described below) with respect to the second lumen 15, and is an opening into which liquid is introduced from a second port 62 described below.

The distal discharge port 17 (refer to FIG. 10) is an opening through which the liquid introduced from the proximal connection port 16 is discharged, and is disposed on the distal end 3a of the sheath 3.

As shown FIGS. 3A, 4, and 5, the third lumen 20 is a lumen into which the knife wire 30 described below is inserted. The third lumen 20 is set such that the knife wire 30 can move forward and backward in the third lumen 20. That is, the third lumen 20 is set so as to have clearance in a state where the knife wire 30 is inserted into the third lumen 20, and the inner diameter of the third lumen 20 is larger than the diameter of the knife wire 30 by the dimensions of the clearance. The third lumen 20 in the pre-curved portion 4 is positioned at a second quadrant Q2 in the virtual coordinate system.

As shown in FIG. 3A, in the state where the pre-curved portion 4 is restored to the curved shape, the second lumen 15 and the third lumen 20 are positioned in a region of an inner surface 401 side of the curved shape, and the first lumen 7 is positioned in a region of an outer surface 402 side of the curved shape. That is, as shown in FIG. 3A, in the vicinity of the distal end 3a of the sheath 3, when viewed from the viewpoint of a dial plate of a timepiece in which the upper side (the upper side of first virtual plane α) of the vertical axis in the virtual coordinate system of the cross section orthogonal to the center axis L1 of the sheath 3 is set to twelve o'clock, the third lumen 20 in the pre-curved portion 4 is positioned between nine o'clock and twelve o'clock.

The third lumen 20 includes a proximal opening portion 21 (refer to FIG. 7), a knife wire accommodation portion 22 (refer to FIG. 14), a first distal communication hole 23, and a second distal communication hole 24.

The proximal opening portion 21 is an opening which communicates with a communication path 57 (refer to FIG. 7) with respect to the third lumen 20, and the knife wire 30 described below is inserted into the proximal opening portion 21.

The knife wire accommodation portion 22 shown in FIG. 14 covers the entire outer circumference of the knife wire 30 so as to maintain the knife wire 30 in an electrically insulated state.

In addition, a drawing portion 5 may be provided on the distal end portion of the pre-curved portion 4, and a copying-deformation portion 6 may be provided on the proximal end portion of the pre-curved portion 4. An outer diameter of the drawing portion 5 has a diameter which is slightly smaller than outer diameters of the base end side and the copying-deformation portion 6 of the sheath 3.

As shown in FIGS. 11 and 14, the first distal communication hole 23 is disposed in a region in which the drawing portion 5 exists in the vicinity of the distal end 3a of the sheath 3. The first distal communication hole 23 is open to the outer circumferential surface 3c of the sheath 3, and communicates with the third lumen 20. The first distal communication hole 23 is positioned at a second quadrant Q2 in the virtual coordinate system. That is, when viewed from the viewpoint of a dial plate of a timepiece in which the upper side (the upper side of first virtual plane α) of the vertical axis in the virtual coordinate system of the cross section orthogonal to the center axis L1 of the sheath 3 is set to twelve o'clock, the first distal communication hole 23 is positioned within a range between nine o'clock and twelve o'clock. That is, the first distal communication hole 23 is formed in an inward side of the bending part of the pre-curved portion 4 and at a position separated from the first virtual plane α.

The second distal communication hole 24 is disposed in the region in which the drawing portion 5 exists in the vicinity of the distal end 3a of the sheath 3. The second distal communication hole 24 is positioned at a position separated from the first distal communication hole 23 so as to be closer to the proximal side relative to the first distal communication hole 23. The second distal communication hole 24 is positioned at the second quadrant Q2 in the virtual coordinate system. That is, similarly to the first distal communication hole 23, the second distal communication hole 24 is formed at the inward side of the bending part of the pre-curved portion 4 and at a position separated from the first virtual plane α. In addition, in the cross section orthogonal to the center axis L1 of the sheath 3, preferably, the positions of the first distal communication hole 23 and the second distal communication hole 24 in the circumferential direction with the center axis L1 of the sheath 3 as a center coincide with each other. However, the positions of the first distal communication hole 23 and the second distal communication hole 24 in the circumferential direction of the sheath 3 do not necessarily need to coincide with each other. The first distal communication hole 23 and the second distal communication hole 24 can exert the functions if the first distal communication hole 23 and the second distal communication hole 24 are provided so as to communicate with the outer circumferential surface 3c of the pre-curved portion 4 positioned at the inward side of the bending part of the pre-curved portion 4, and are open to extend in the direction separated from the outside in the radial direction from the position of the third lumen 20 with respect to the center axis L1 of the sheath 3.

The knife wire 30 has a function which incises a target portion to be treated.

The knife wire 30 includes a core wire 31 having conductivity, and an insulating film 32 which covers the core wire 31. In addition, the knife wire 30 includes a capacity transmission portion 33, an incision portion 34, and a distal fixing member (fixing portion) 37 in this order from the proximal side.

For example, the insulating film 32 is formed by coating resins such as polytetrafluoroethylene (PTFE), tetrafluoro-ethylene-hexafluoropropylene resin (FEP), polyethylene, polyolefin, polyamide, vinyl chloride, latex, natural rubber, polysulfone, polyphenylsulfon, polyetherimide, POM, PEEK, polycarbonate, or ABS, or combined resin materials thereof on the outer surface of the core wire 31.

As shown in FIG. 11, the incision portion 34 is a portion in which the core wire 31 is not covered by the insulating film 32 (refer to FIG. 13) over the entire length of the knife wire 30 and which is disposed outside the sheath 3. The incision portion 34 can incise tissues by energizing a high-frequency current supplied to the core wire 31 via a connector 73 (refer to FIG. 2) described below. The incision portion 34 includes a curved knife portion 35 and a bending portion 36.

As shown in FIGS. 13 and 14, the capacity transmission portion 33 is a portion which is positioned from the proximal end 30b which is fixed to a slider portion 71 of a handle portion 67 in the operation portion 40 (refer to FIG. 2) described below to the base end side of the incision portion 34 in the entire length of the knife wire 30. In the capacity transmission portion 33, the core wire 31 is covered with the insulating film 32. In a state where the knife wire 30 is inserted into the third lumen 20 and is fixed to the third lumen 20 by the distal fixing member 37, the distal end of the capacity transmission portion 33 is positioned in the vicinity of the second distal communication hole 24.

As shown in FIGS. 11, 12, and 13, the curved knife portion 35 is disposed at the inward side of the bending part of the pre-curved portion 4 at the second quadrant Q2 in the virtual coordinate system in the region between the first distal communication hole 23 and the second distal communication hole 24. The curved knife portion 35 is curved between the first distal communication hole 23 and the second distal communication hole 24. The bending portion 36 may be provided on the distal end 35a of the curved knife portion 35.

The bending portion 36 has a shape which is bent in the direction approximately parallel with a tangential line to the outer circumferential surface 3c of the sheath 3 at the second quadrant Q2 in the virtual coordinate system defined by the first virtual plane α and the second virtual plane β. Specifically, the incision portion 34 has the bending portion 36 having a shape which is bent in the direction separated from the first plane α in the extension direction of the first distal communication hole 23 at the position protruding from the first distal communication hole 23.

In the knife wire 30, the bending portion 36 is a portion in which the core wire 31 is bent such that the core wire 31 extending from the curved knife portion 35 toward the distal end 30a of the knife wire 30 is curved toward the first distal communication hole 23. The bending portion 36 may be covered with the insulating film 32.

The distal fixing member 37 is provided in the distal end 30a of the knife wire 30, and is fixed to the inner portion of the third lumen 20. That is, in the state where the distal fixing member 37 is inserted into the pre-curved portion 4, the knife wire 30 and the pre-curved portion 4 are fixed to each other by the distal fixing member 37. In addition, the distal fixing member 37 is connected to an inner circumferential surface 20c of the third lumen 20 in the pre-curved portion 4 by friction, bonding, or other connection methods. Since the distal fixing member 37 is fixed to the inner portion of the third lumen 20 (pre-curved portion 4), the distal portion of the knife wire 30 is not extracted from the first distal communication hole 23.

The operation portion 40 shown in FIG. 2 is a portion which is held by an operator, and is disposed on the proximal end 2b (proximal end 3b of sheath 3) of the insertion portion 2. Various operations for operating the treatment tool 1 for an endoscope are input to the operation portion 40.

The operation portion 40 includes a distal configuration portion 41, a flexible connection portion 58, a proximal configuration portion 61, and a handle portion 67.

As shown in FIG. 6, the distal configuration portion 41 is a member which is disposed on the most distal side in the operation portion 40.

The distal configuration portion 41 includes a main body portion 42, a connection portion 45 with respect to the endoscope apparatus 100, and a connection portion 48 with respect to the sheath 3.

As shown in FIG. 7, the main body portion 42 is a hard member, and includes a main body side liquid-feeding pipeline 43 and a main body side wire passage 44 inside the main body portion 42. The main body portion 42 is connected to the first port 49 described below in the connection portion 48, and extends in a radial direction (straight-line direction intersecting a longitudinal axis L2) with respect to the longitudinal axis L2 of the first port 49. In the present embodiment, the main body portion 42 extends to the proximal end 48b of the connection portion 48 along a virtual plane which includes the longitudinal axis L2 of the first port 49 and a short axis orthogonal to the longitudinal axis L2.

The main body side liquid-feeding pipeline 43 forms a portion of a pipeline which communicates with the second port 62 (refer to FIG. 20) described below and the second lumen 15.

The main body side wire passage 44 is a passage into which the capacity transmission portion 33 of the knife wire 30 inserted into the third lumen 20 is inserted so as to move forward and backward.

The connection portion 45 with respect to the endoscope apparatus 100 includes a hook 46 and an extension portion 47. The hook 46 is a locking portion which can be locked to the holding portion 102 (refer to FIG. 19) which is provided in the endoscope apparatus 100. The extension portion 47 connects the hook 46 and the main body portion 42.

The hook 46 is an elastic member which is formed in a C shape so as to surround a portion of the outer circumferential surface of the holding portion 102 which is provided in the endoscope apparatus 100. The hook 46 can press the outer surface of the holding portion 102 of the endoscope apparatus 100 by a restoring force by which the hook 46 is restored to a C shape. As a result, the hook 46 engages with the holding portion 102 of the endoscope apparatus 100.

The extension portion 47 is a hard rod-shaped member which connects the main body portion 42 and the hook 46. A proximal end 47b of the extension portion 47 is coupled to the main body portion 42, and a distal end 47a of the extension portion 47 is coupled to the hook 46. The extension portion 47 holds the hook 46 so as to be closer to the distal side relative to the main body portion 42.

The connection portion 48 with respect to the sheath 3 is an approximately tubular shape into which the proximal end 3b of the sheath 3 and the vicinity thereof are inserted. The connection portion 48 with respect to the sheath 3 extends from the main body portion 42 in the direction of the distal end in a state of having a gap between the connection portion 48 and the extension portion 47. The connection portion 48 is installed so as to be parallel with the main body portion 42 and the extension portion 47. Accordingly, an operator holds the main body portion 42 and the extension portion 47, and thus, it is possible to easily and precisely control the direction of the first port 49 without interfering with the visibility of the connection portion 48 and the first port 49 and the insertion of the guide wire 80 described below.

The connection portion 48 with respect to the sheath 3 includes the first port 49, the communication path 56 with respect to the second lumen 15, and the communication path 57 with respect to the third lumen 20.

The operation portion 40 (connection portion 48) includes a tubular portion 76, shown in FIG. 8, which is framed in an approximately tubular shape having an inner diameter portion into which the proximal end 3b of the sheath 3 and the vicinity thereof can be inserted, and the first port 49 which is connected from the inner circumferential surface of the tubular portion to the outer circumferential surface and has an opening into which the guide wire 80 can be inserted. In addition, a port-fixing portion 77, shown in FIG. 8, which fixes the first port 49 to the sheath 3 is disposed on the proximal end 3b of the sheath 3 and in the vicinity thereof such that the opening of the opening portion of the first port 49 and the opening direction of the inlet portion 8 coincide with other. The port-fixing portion can appropriately adopt known fixing methods such as direct adherence between the sheath 3 and the first port 49, a method in which a slit is formed in the sheath 3 and the first port 49 is mechanically locked to the slit, or the like. As a result, the sheath 3 is not rotated around the longitudinal axis and is not extracted from the tubular portion.

As shown in FIGS. 6, 8, and 9B, the first port 49 is a port which becomes an inlet through which the guide wire 80 (refer to FIG. 28) is introduced into the first lumen 7. The opening of the first port 49 includes an inner opening edge portion 50 and an outer opening edge portion 51. Preferably, the first port 49 includes a taper portion 52, and a notch portion 55 (also shown by the double-headed arrow N in FIG. 8) which communicates with the opening portion.

As shown in FIGS. 8 and 9B, the inner opening edge portion 50 forms a contour of an opening which is open to the inner circumferential surface of the tubular portion. In addition, the inner opening edge portion 50 includes a contour line which coincides with the contour of the inlet portion 8 formed on the proximal portion of the sheath 3, or a contour line which surrounds the contour of the inlet portion 8. That is, the contour of the opening of the inner opening edge portion 50 is formed such that the edge (opening edge portion) of the inlet portion 8 of the sheath 3 approximately coincides with a projection portion which is projected on the inner circumferential surface of the first port 49 from the opening direction (the direction along the straight line orthogonal to the center axis of the first lumen 7 and the center axis of the sheath 3), or surrounds (is positioned so as to be closer the outside relative to the edge of the inlet portion 8) the projection portion. The inner opening edge portion 50 is disposed at the position at which the inner opening edge portion 50 can come into contact with the outer circumferential surface 3c of the sheath 3. According to the above-described positional relationship, the sheath 3 is fixed to the operation portion 40.

The outer opening edge portion 51 forms a contour of an opening which is open to the outer circumferential surface of the tubular portion. In addition, the outer opening edge portion 51 is positioned outside further in the radial direction of the sheath 3 relative to the inner opening edge portion 50. The outer opening edge portion 51 has a larger opening area than the opening area which is defined by the inner opening edge portion 50. The outer opening edge portion 51 includes a contour line which approximately coincides with the outer circumference of the contour of the inlet portion 8 formed on the proximal portion of the sheath 3, or a contour line which surrounds the contour of the inlet portion 8. When viewed from the direction perpendicular to the surface defined by the inner opening edge portion 50, the contour of the outer opening edge portion 51 is positioned outside the inner opening edge portion 50.

The above-described port-fixing portion is fixed in a state where the first port 49 is positioned in the direction around the longitudinal axis of the sheath 3 and in the longitudinal direction of the sheath 3 such that the contours of the openings of the inner opening edge portion and the outer opening edge portion approximately coincide with the projection portion in which the edge of the inlet portion 8 of the sheath 3 is projected in the opening direction or surrounds the projection portion.

Each of the inner opening edge portion 50 and the outer opening edge portion 51 is formed in an elliptical shape having the longitudinal axis L2 in a straight-line direction in which the distal end 48a of the connection portion 48 with respect to the sheath 3 and the proximal end 48b of the connection portion 48 with respect to the sheath 3 are connected to each other.

The inner opening edge portion 50 and the outer opening edge portion 51 define the opening shape of the first port 49. The length in the longitudinal axis L2 direction of the opening of the first port 49 can be adjusted corresponding to the distal end 80a of the guide wire 80 which can be inserted into the first port 49.

Figure 15:
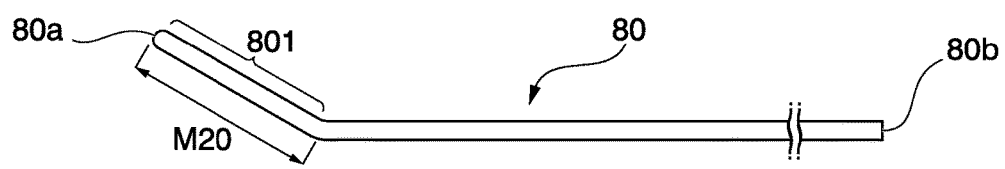
FIG. 15 is a side view showing a configuration example of a guide wire which is used along with the treatment tool for an endoscope according to the first embodiment of the present invention.
Figure 16:
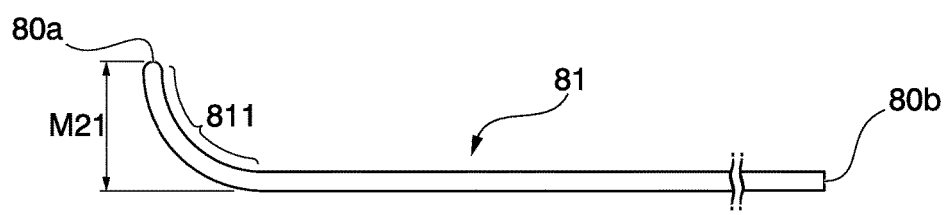
FIG. 16 is a side view showing another configuration example of the guide wire which is used along with the treatment tool for an endoscope according to the first embodiment of the present invention.

FIG. 15 is a side view showing a configuration example of the guide wire 80 which is used along with the treatment tool 1 for an endoscope. FIGS. 16 to 17B are side views showing guide wires 81, 82, and 83 of other configuration examples of the guide wire 80 shown in FIG. 15.

As shown in FIGS. 15 to 17B, as the guide wires 80, 81, 82, and 83 which are inserted into the first port 49, known configurations may be appropriately adopted. For example, as shown in FIGS. 16 and 17A, curved shape portions 811 and 812 may be provided in which at least a portion of the proximal region (distal portion) of the distal end 80a of each of the guide wires 81 and 82 has a curved shape. Each of the curved shape portions 811 and 812 has a shape which is curved so as to form a portion of an arc. For example, as shown in FIG. 17A, the guide wire 82 may be adopted which has a shape in which the curved shape portion 812 of the proximal region of the distal end 80a is curved in a semi-arc shape such that the distal end 80a faces the proximal direction of the guide wire 82. In addition, the proximal region (distal portion) of the distal end 80a of each of the guide wires 80 and 83 may have a bending portion which has a restoring force by which the center axis of each of the guide wires 80 and 83 is restored so as to be a bias shape. For example, as shown in FIGS. 15 and 17B, the distal portion is provided on the distal side of each of the guide wires 80 and 83 relative to the bending portion, and the bending portion may have a shape which is bent such that the distal portion of each of the guide wires 80 and 83 extends in a direction in which an obtuse angle, a right angle, or an acute angle is formed with respect to the proximal portion of each of the guide wires 80 and 83. Angle type guide wires 80, 81, 82, and 83 are excellent in that an operation is easily performed when the distal end 80a of each of the guide wires 80, 81, 82, and 83 is inserted into a desired lumen inside a lumen structure in which traveling is complicated or a lumen structure having branches.

In addition, in FIGS. 15 and 17B, the lengths of the distal portions of the guide wires 80 and 83 are respectively represented by the M20 and M23. Moreover, in FIGS. 16 and 17A, maximum lengths in tangential directions on the tips of the curved shape portions 811 and 812 of the guide wires 81 and 82 are respectively represented by M21 and M22.

Figure 18:
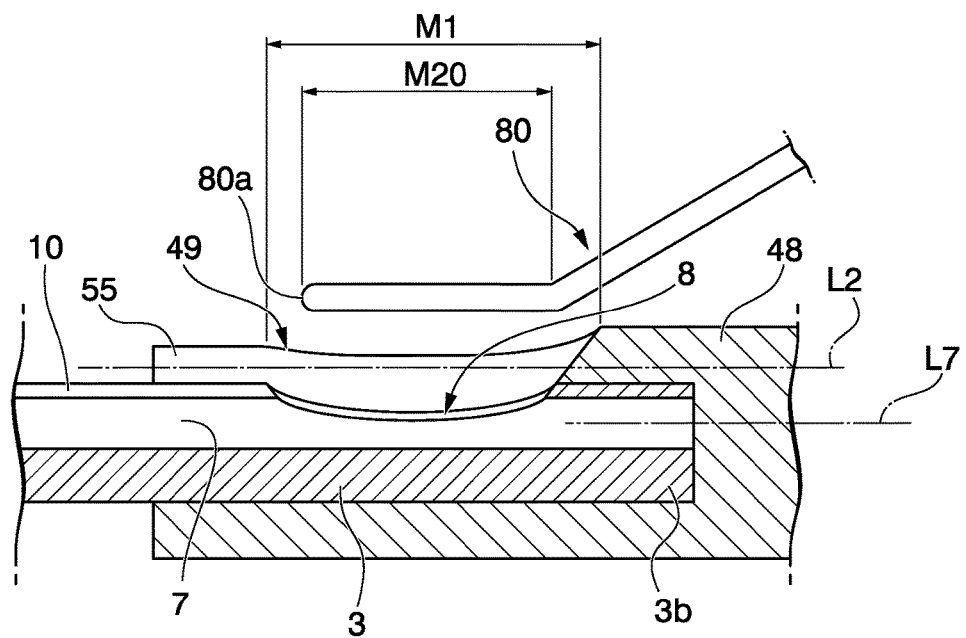
FIG. 18 is a sectional view showing an aspect in which the guide wire is inserted into a first port of the treatment tool for an endoscope according to the first embodiment of the present invention.

FIG. 18 is a view for explaining a relationship between the shape of the first port 49 and the shape of the guide wire 80 in the treatment tool 1 for an endoscope.

As shown in FIG. 18, a length M1 of the opening of the first port 49 in the longitudinal axis direction of the sheath 3 may be approximately the same as a length M20 of the distal portion of the guide wire 80, or may be slightly longer than the length M20.

In a case where the guide wire 81 shown in FIG. 16 is adopted, the length M1 of the opening of the first port 49 in the longitudinal axis direction of the sheath 3 may be set so as to be approximately the same as the maximum M21 of the component in the tangential direction on the tip of the curved shape portion 811, or may be set so as to be slightly longer than the maximum length M21.

Figure 17A:
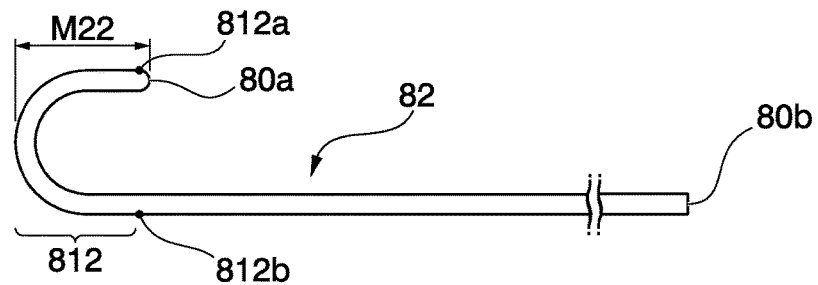
FIG. 17A is a side view showing still another configuration example of the guide wire which is used along with the treatment tool for an endoscope according to the first embodiment of the present invention.
Figure 17B:
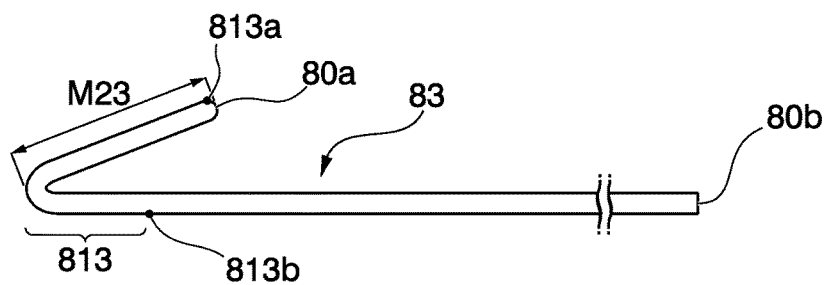
FIG. 17B is a side view showing still another configuration example of the guide wire which is used along with the treatment tool for an endoscope according to the first embodiment of the present invention.

In a case where the guide wire 82 shown in FIG. 17A is adopted, the length M1 of the opening of the first port 49 in the longitudinal axis direction of the sheath 3 may be set so as to be approximately the same as the maximum M22 of the component in the tangential direction on the tip of the curved shape portion 812, or may be set so as to be slightly longer than the maximum length M22.

In a case where the guide wire 83 shown in FIG. 17B is adopted, the length M1 of the opening of the first port 49 in the longitudinal axis direction of the sheath 3 may be set so as to be approximately the same as the length M23 of the distal portion of the guide wire 83, or may be set so as to be slightly longer than the length M23.

As shown in FIGS. 8, 9A, and 9B, the taper portion 52 includes a distal taper surface 53 and a proximal taper surface 54. The distal taper surface 53 is smoothly connected to the notch portion 55 on the distal end 49a portion of the first port 49. The proximal taper surface 54 is a taper surface which connects the inner opening edge portion 50 and the outer opening edge portion 51 on the proximal end 49b of the first port 49 and the side portions connected to both the ends of the first port 49.

The distal taper surface 53 guides the guide wire 80 so as to move in the distal end 3a direction of the sheath 3 from the first port 49 via the notch portion 55 when the guide wire 80 is inserted into the first lumen 7 of the sheath 3 through the first port 49.

The proximal taper surface 54 guides the distal end 80a of the guide wire 80 into the first lumen 7 of the sheath 3 when the distal end 80a of the guide wire 80 is inserted from the outside of the connection portion 48 with respect to the sheath 3 into the first port 49.

The first port 49, on which the taper portion 52 is formed, is disposed on the outer circumferential portion of the inlet portion 8 in a state where the inlet portion 8 of the first lumen 7 is exposed to the outside such that the inner surface 7c of the first lumen 7 can be viewed from the outside of the connection portion 48 with respect to the sheath 3.

Figure 19:
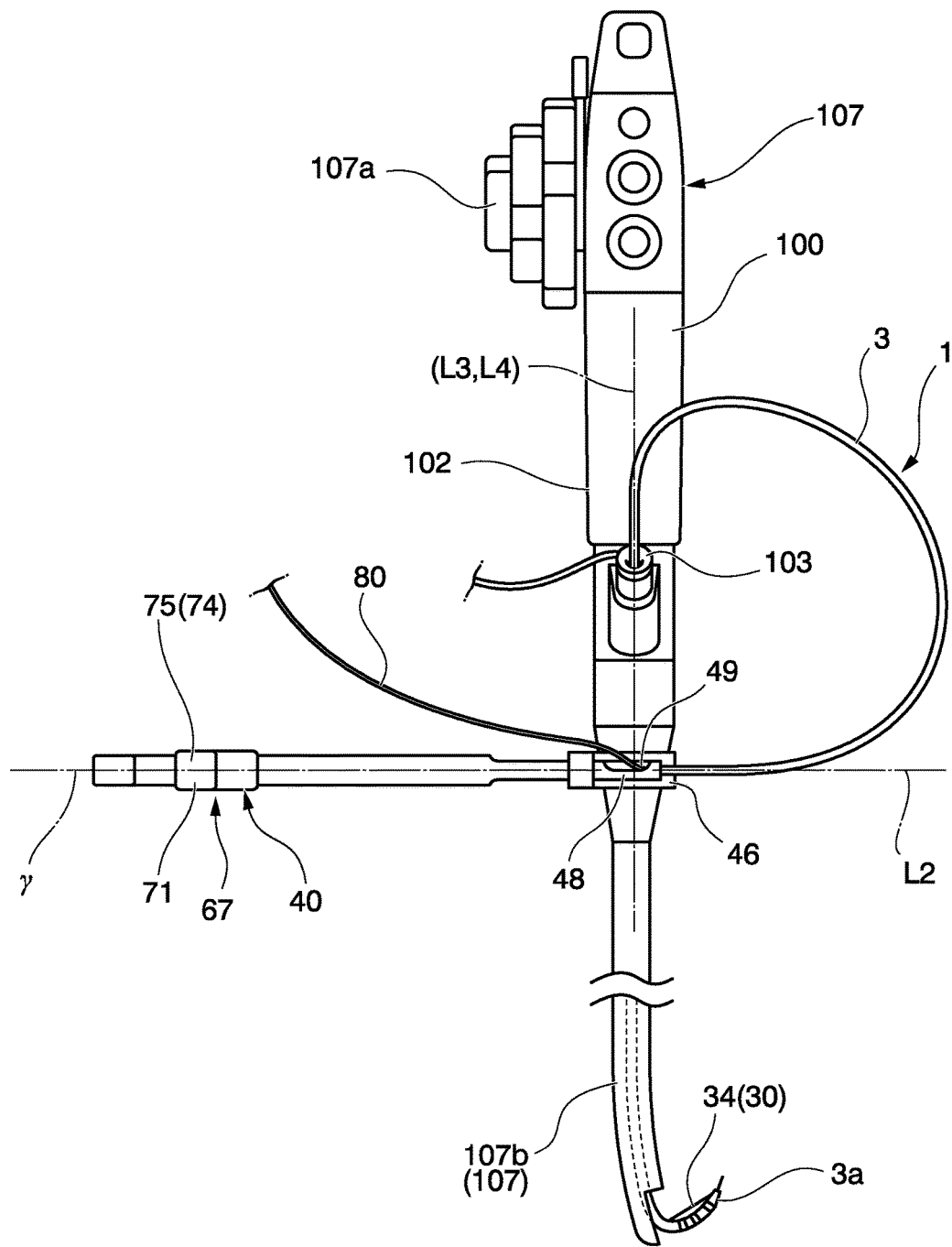
FIG. 19 is a view showing a positional relationship between the first port and the operation portion in a state where the treatment tool for an endoscope according to the first embodiment of the present invention is attached to an endoscope apparatus.
Figure 20:
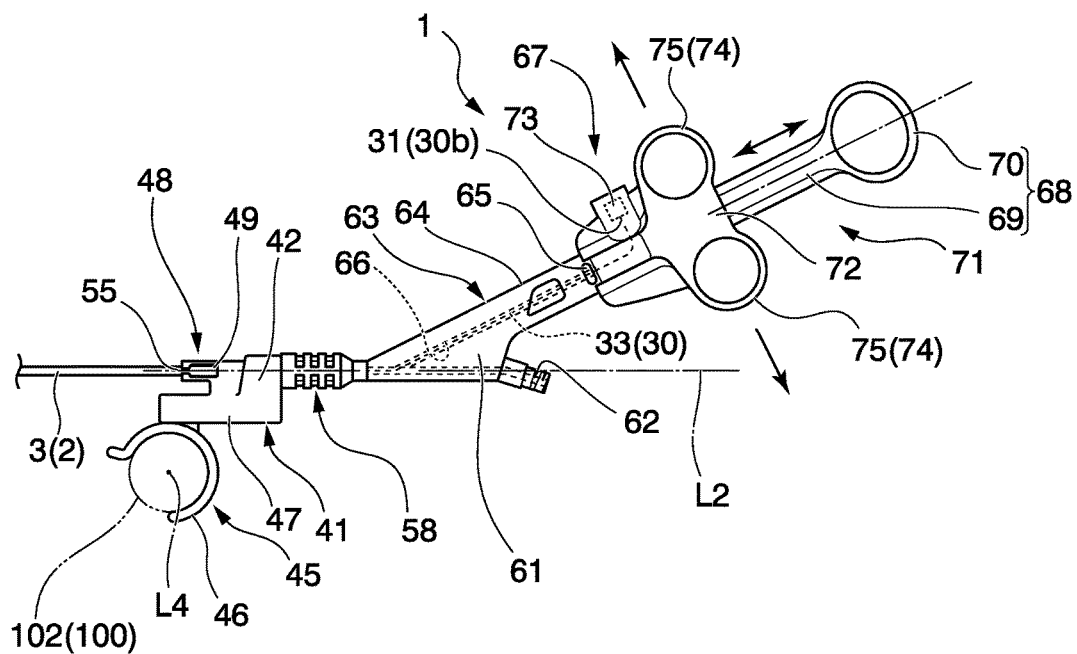
FIG. 20 is a view showing a positional relationship between a hook and the first port in a state where the treatment tool for an endoscope according to the first embodiment of the present invention is attached to the endoscope apparatus.

FIG. 19 is a view showing a positional relationship between the first port 49 and the operation portion 40 in a state where the treatment tool 1 for an endoscope is attached to the endoscope apparatus 100. FIG. 20 is a view showing a positional relationship between the hook 46 and the first port 49 in the state where the treatment tool 1 for an endoscope is attached to the endoscope apparatus 100.

As shown in FIG. 19, in a state where the operation portion 40 is locked to the holding portion 102 of the endoscope apparatus 100 by the hook (locking portion) 46, the positional relationship between the opening of the first port 49 and the hook 46 is determined such that the opening of the first port 49 faces the bending operation section 107a side of the endoscope apparatus 100. Here, the bending operation section 107a side is an operation portion capable of actively operating a bending deformation portion 107b which is provided on the tip portion of the endoscope apparatus 100. In the first port 49, a through-hole may be formed, which has an axis direction, which intersects a virtual plane penetrating along an axis approximately parallel with the longitudinal direction of the holding portion 102, as a penetrating direction (axis direction). The treatment tool 1 for an endoscope may be fixed to the endoscope apparatus 100 so as to extend in a direction approximately parallel with a direction in which a forceps plug 103 of the endoscope apparatus 100 extends, and in this case, the axis direction (center axis L3 direction described below) in which the through-hole of the first port 49 penetrates has a positional relationship which is twisted with respect to the longitudinal axis of the holding portion 102 of the endoscope apparatus 100.

In the present embodiment, in the opening of the first port 49, a straight-line direction (refer to FIG. 8) (hereinafter, referred to as a "center axis L3 direction of the opening of the first port 49") from the surface defined by the inner opening edge portion 50 toward the surface defined by the outer opening edge portion 51 is approximately parallel with a center axis L4 direction of a circle surrounding the holding portion 102 in the hook 46, as shown in FIG. 20. That is, in the cross section of the operation portion 40 of the treatment tool 1 for an endoscope shown in FIG. 9A, the center axis L3 direction of the opening of the first port 49 passing through a portion between the inner opening edge portions 50 and a portion between outer opening edge portions 51 through a center axis L7 of the first lumen 7 is approximately parallel with the center axis L4 direction of the circle surrounding the holding portion 102 in the hook 46. As a result, as shown in FIG. 9A, the opening of the first port 49 is formed so as to be open with the center axis L3 of the opening of the first port 49 orthogonal to the center axis L1 of the sheath 3 as the center, and the center axis L3 of the opening of the first port 49 is approximately parallel with the center axis L4 of the circle surrounding the holding portion 102 of the endoscope apparatus 100. Accordingly, in the state where the operation portion 40 is attached and locked to the endoscope apparatus 100 by the hook 46, the opening of the first port 49 faces the direction (refer to FIG. 24) which is visible by an operator in a general positional relationship in which the operator holds the holding portion 102 of the endoscope apparatus 100 so as to operate the endoscope apparatus 100. Therefore, when an operator who operates the endoscope apparatus 100 cooperatively operates the treatment tool, the operator of the endoscope apparatus 100 easily views the opening portion.

As shown in FIGS. 8 and 9A, the notch portion 55 is a portion in which a notch is formed so as to have an approximately C shape when the connection portion 48 is viewed from the cross section orthogonal to the center axis L1 of the sheath 3. The notch portion 55 has a gap in which the diameter of the connection portion 48 is larger than the diameter of the guide wire 80 by clearance through which the guide wire 80 can move such that the guide wire 80 can move from the inlet portion 8 to the slit portion 10. The gap in the notch portion 55 is provided along the slit portion 10 of the sheath 3. The notch portion 55 has an inner surface 55c which can come into contact with the outer circumferential surface 3c of the sheath 3, and holds the outer circumferential surface 3c of the sheath 3.

As shown in FIG. 7, since the notch portion 55 is provided so as to be separated from the extension portion 47 in the connection portion 45 with respect to the endoscope apparatus 100, the notch portion 55 is configured such that external force transmitted from the endoscope apparatus 100 via the hook 46 is not easily transmitted to the notch portion 55. In the present embodiment, both of the notch portion 55 and the distal portion of the first port 49 are separated from the extension portion 47.

As shown in FIG. 7, the communication path 56 with respect to the second lumen 15 communicates with the second lumen 15 of the sheath 3, and the communication path 57 with respect to the third lumen 20 communicates with the third lumen 20 of the sheath 3.

As shown in FIGS. 2 and 7, the flexible connection portion 58 is a member which connects the distal configuration portion 41 and the proximal configuration portion 61, and has flexibility. The flexible connection portion 58 buffers twisting generated between the distal configuration portion 41 and the proximal configuration portion 61. That is, in a case where the operation portion 40 and the endoscope apparatus 100 are connected to each other by the hook 46, the flexible connection portion 58 buffers the twisting which is generated between the distal configuration portion 41 and the proximal configuration portion 61 due to the operation of the operation portion 40 and the operation of the endoscope apparatus 100.

As shown in FIG. 7, the flexible connection portion 58 includes a liquid-feeding communication passage 59 and a knife wire communication passage 60 inside the flexible connection portion 58. The liquid-feeding communication passage 59 communicates with the second lumen 15. The knife wire communication passage 60 communicates with the third lumen 20.

As shown in FIG. 2, the proximal configuration portion 61 includes the second port 62 and a connection portion 63 with respect to the handle portion 67.

The second port 62 is a port to which a syringe or the like in which liquid is accommodated is connected. For example, in a procedure in which a contrast agent is discharged from the distal end 3a of the sheath 3 through the second lumen 15, a syringe which is filled with the contrast agent is connected to the second port 62. A proximal end 62b of the second port 62 has a connector structure which can be connected to the syringe having a Luer-lock structure. A distal end 62a of the second port 62 communicates with the liquid-feeding communication passage 59 (refer to FIG. 7) which is formed in the flexible connection portion 58.

As shown in FIG. 20, the connection portion 63 with respect to the handle portion 67 includes a handle-fixing portion 64 and a knife wire passage 66. The handle-fixing portion 64 is provided so as to fix the handle portion 67 in a predetermined connection state. The knife wire passage 66 communicates with the knife wire communication passage 60 in the flexible connection portion 58.

The handle-fixing portion 64 has a claw structure 65 which can lock the distal end of the shaft portion 68 of the handle portion 67. Instead of providing the handle-fixing portion 64, the proximal configuration portion 61 and the shaft portion 68 may be integrally molded.

The handle-fixing portion 64 has a rod shape which extends in the direction which is inclined with respect to the longitudinal axis L2 direction of the first port 49. Specifically, the handle-fixing portion 64 has a rod shape, and has a center axis L5 which is inclined so as to be gradually separated from the longitudinal axis L2 of the first port 49 from the distal end 64a of the handle-fixing portion 64 toward the proximal end 64b of the handle-fixing portion 64.

The knife wire passage 66 is a passage into which the capacity transmission portion 33 of the knife wire 30 is inserted so as to move forward and backward. A distal end 66a of the knife wire passage 66 communicates with the proximal end of the knife wire communication passage 60 (refer to FIG. 7) in the flexible connection portion 58. The proximal end 66b of the knife wire passage 66 communicates with the inner portion of the shaft portion 68 of the handle portion 67.

Inputs for operating the knife wire 30 are applied to the handle portion 67 by an operator. The handle portion 67 includes a shaft portion 68 and a slider portion 71. The shaft portion 68 is fixed to the handle-fixing portion 64 of the proximal configuration portion 61. The slider portion 71 is connected to the shaft portion 68.

The shaft portion 68 includes a rod-shaped portion 69 and a ring portion 70. The rod-shaped portion 69 extends so as to be coaxial with a center axis L5 (refer to FIG. 24) of the handle-fixing portion 64 or so as to be linear along the center axis L5 of the handle-fixing portion 64. The ring portion 70 is formed on the proximal end of the rod-shaped portion 69.

The rod-shaped portion 69 is a portion to which the slider portion 71 described below is attached. The connector 73 of the slider portion 71 and the proximal portion of the knife wire 30 are disposed inside the rod-shaped portion 69.

The ring portion 70 is an annular portion through which fingers of an operator can pass.

The slider portion 71 includes a moving body 72, the connector 73, and a finger-hooking portion 74. The moving body 72 is connected to the shaft portion 68 so as to move forward and backward. The connector 73 can be connected to a high-frequency power supply device. Two rings 75 through which fingers of an operator can pass are formed on the finger-hooking portion 74.

The moving body 72 can move forward and backward in the longitudinal direction of the shaft portion 68.

The connector 73 is fixed to the moving body 72, and is fixed to the proximal end 33b of the capacity transmission portion 33 of the knife wire 30. The connector 73 is formed of a conductor, and is electrically connected to the core wire 31 of the knife wire 30.

An operator causes his/her fingers to pass through the two rings 75, causes his/her fingers to pass through the ring portion 70 of the rod-shaped portion 69, and opens and closes his/her hands. Accordingly, the operator can use the finger-hooking portion 74 so as to move the moving body 72 forward and backward with respect to the rod-shaped portion 69. The finger-hooking portion 74 protrudes toward the outside (direction away from the center axis L5) from the outer surface of the moving body 72. As shown in FIG. 19, the protrusion direction of the finger-hooking portion 74 from the outer surface of the moving body 72 has only not to be in a plane including the center axis L3 direction of the opening of the first port 49. Preferably, the protrusion direction of the finger-hooking portion 74 from the outer surface of the moving body 72 is a direction of a plane (hereinafter, referred to as a "ring extension plane γ") orthogonal to the center axis L3 direction of the opening portion of the first port 49. According to this configuration, the finger-hooking portion 74 does not easily interfere with the portion of the guide wire 80 outside of the first port 49, wherein the guide wire 80 is introduced into the first lumen 7 through the first port 49.

Figure 21:
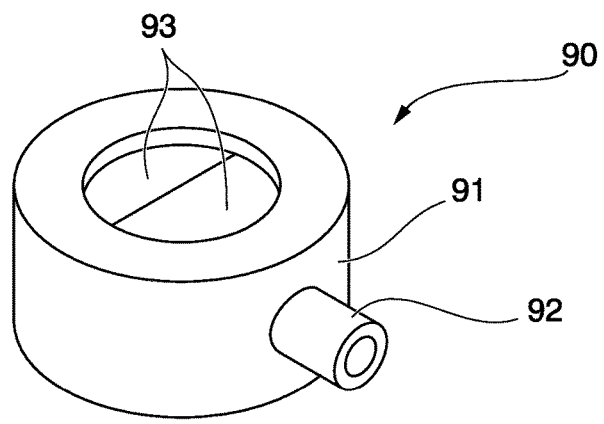
FIG. 21 is a perspective view showing a treatment tool attachment-assisting instrument which can be attached to the endoscope apparatus according to the first embodiment of the present invention.
Figure 22:
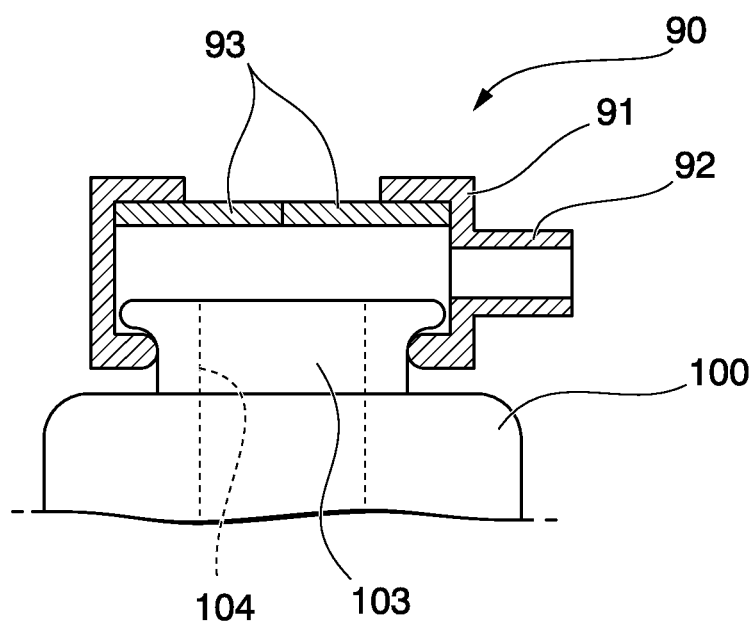
FIG. 22 is a partial sectional view showing an internal structure of the treatment tool attachment-assisting instrument shown in FIG. 21.

Next, a configuration of a treatment tool attachment-assisting instrument 90 will be described, which can be used in the procedure in which the treatment tool 1 for an endoscope according to the present embodiment is attached to the endoscope apparatus 100. FIG. 21 is a perspective view showing the treatment tool attachment-assisting instrument 90 which can be attached to the endoscope apparatus 100. FIG. 22 is a partial sectional view showing an internal structure of the treatment tool attachment-assisting instrument 90.

As shown in FIGS. 21 and 22, the treatment tool attachment-assisting instrument 90 includes an assisting instrument main body 91, a discharge tube 92, and a plug body 93. The assisting instrument main body 91 has a tubular shape which can be fixed to the forceps plug 103 of the endoscope apparatus 100. The discharge tube 92 communicates with the internal space of the assisting instrument main body 91. The plug body 93 is disposed on the extension line of the center axis of the treatment tool channel 104 from the proximal opening of the treatment tool channel 104 in the forceps plug 103.

The assisting instrument main body 91 has an attachment structure which can be water-tightly connected to the forceps plug 103. The discharge tube 92 can be connected to a pipeline which is connected to a liquid-discharge container (not shown). The plug body 93 is a soft member which has an opening or a gap through which the plug body 93 can come into close contact with the outer circumferential surface 3c of the sheath 3.

Figure 24:
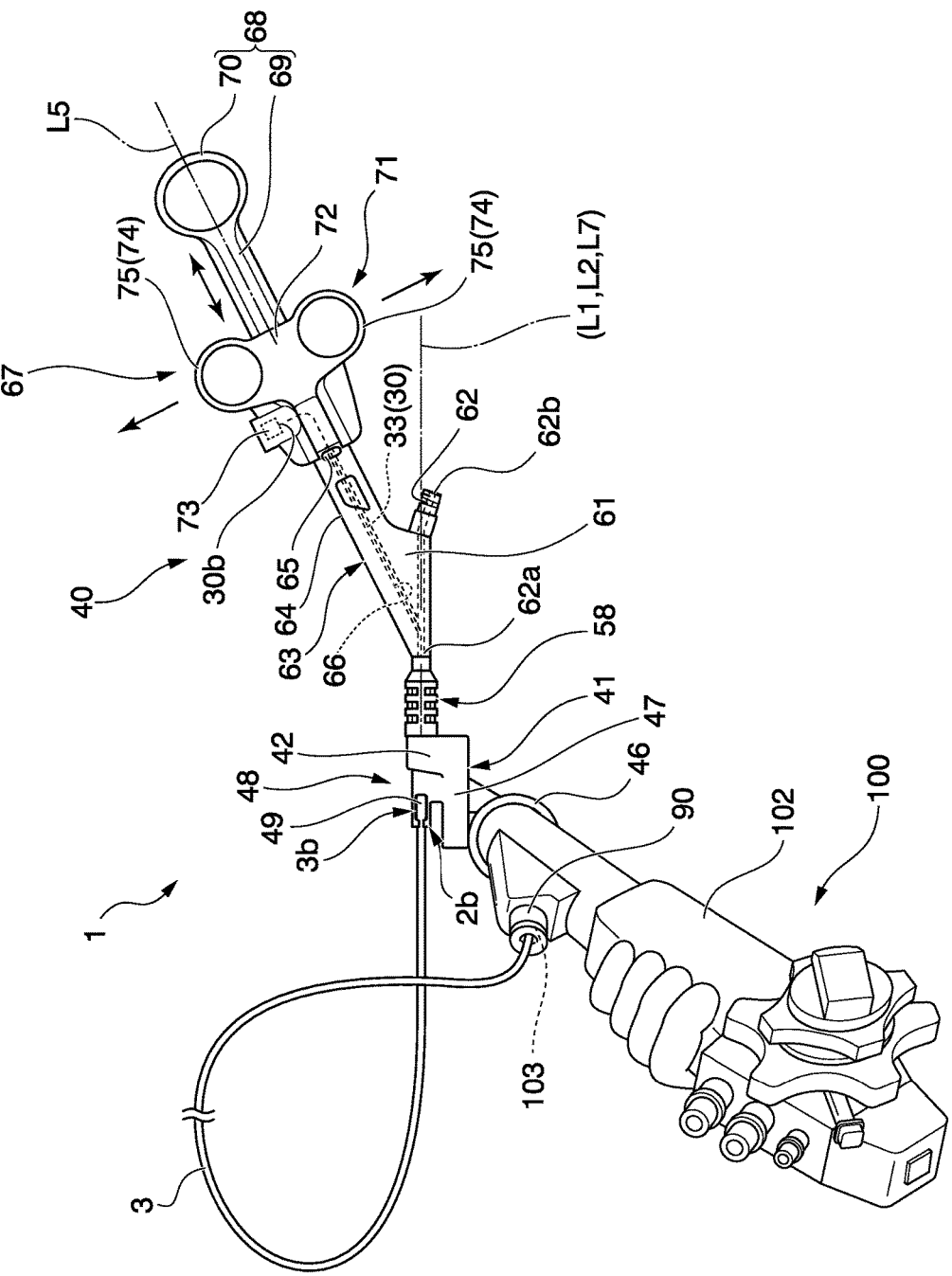
FIG. 24 is a view when the state where the treatment tool for an endoscope according to the first embodiment of the present invention is attached to the endoscope apparatus is viewed from a viewpoint of an operator of the endoscope apparatus.

In the present embodiment, the treatment tool attachment-assisting instrument 90 is fixed to the forceps plug 103 of the endoscope apparatus 100 before the treatment tool 1 for an endoscope is inserted into the treatment tool channel 104 (refer to FIG. 24). In the state where the treatment tool attachment-assisting instrument 90 is attached to the forceps plug 103, liquid, which flows in reverse from the distal side of the treatment tool channel 104 of the endoscope apparatus 100 toward the proximal side thereof, mainly flows through the discharge tube 92. Accordingly, the liquid, which flows in reverse from the distal side of the treatment tool channel 104 of the endoscope apparatus 100 toward the proximal side thereof, is very unlikely to leak from the plug body 93 to the outside of the treatment tool attachment-assisting instrument 90.

Next, the operation of the treatment tool 1 for an endoscope according to the present embodiment will be described. In the present embodiment, an example is shown in which the treatment tool 1 for an endoscope according to the present embodiment is used along with the endoscope apparatus 100 in a case where endoscopic sphincterotomy (EST), endoscopic retrograde cholangiopancreatography (ERCP), and calculus removal are sequentially performed as a series of procedures.

Figure 23:
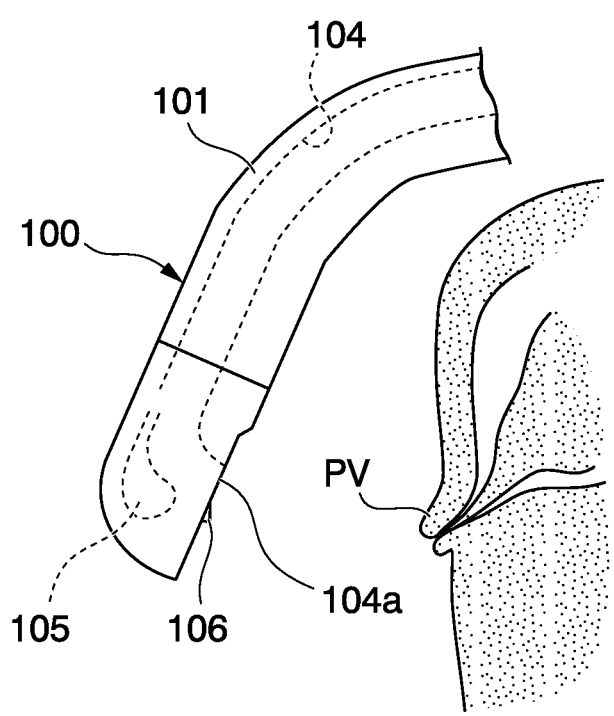
FIG. 23 is a view showing a process when the treatment tool for an endoscope according to the first embodiment of the present invention is used.

FIG. 23 is a view showing a process when the treatment tool 1 for an endoscope is used.

As shown in FIGS. 1 and 23, in the present embodiment, a side view type endoscope apparatus 100 which is suitable for observing a duodenal papilla PV is used.

For example, the side view type endoscope apparatus 100 includes a tubular member 101, a holding portion 102, a forceps plug 103, a treatment tool channel 104, a raising stand 105, and an imaging portion 106. The tubular member 101 is a portion which is inserted into the body. The holding portion 102 is disposed on the proximal end of the tubular member 101. The forceps plug 103 is disposed on a portion of the holding portion 102. The treatment tool channel 104 communicates with the forceps plug 103 and is disposed inside the tubular member 101. The raising stand 105 is provided so as to be movable in an opening portion from which the treatment tool protrudes in order to change the direction of the treatment tool or the like protruding from the treatment tool channel 104 on the distal end 104a of the treatment tool channel 104 to the direction orthogonal to a center axis L8 of the tubular member 101. The imaging visual field of the imaging portion 106 faces the direction orthogonal to the center axis L8 of the tubular member 101. The imaging portion 106 is provided so as to be adjacent to the opening portion from which the treatment tool protrudes.

The side view type endoscope apparatus 100 of the present embodiment includes a bending mechanism 107 (refer to FIG. 1). The bending mechanism 107 includes the bending operation section 107a and bending deformation portion 107b to operate to bend the distal portion of the tubular member 101.

The treatment tool 1 for an endoscope according to the present embodiment can be suitably used for both of an aspect in which an operator of the endoscope apparatus 100 and an operator of the treatment tool 1 for an endoscope are different from each other, and an aspect in which the hook 46 is connected to the holding portion 102 of the endoscope apparatus 100 and one operator operates the endoscope apparatus 100 and the treatment tool 1 for an endoscope.

First, a case where the hook 46 is connected to the holding portion 102 of the endoscope apparatus 100 shown in FIG. 1 so as to use the treatment tool 1 for an endoscope will be described.

First, in a state where the treatment tool 1 for an endoscope is not attached to the endoscope apparatus 100, as shown in FIG. 23, according to the known procedure, an operator guides the endoscope apparatus 100 to the duodenal papilla PV which is the target portion to be treated and observes the target portion to be treated using the endoscope apparatus 100. At this time, the treatment tool attachment-assisting instrument 90 may be attached to the forceps plug 103, and may not be attached to the forceps plug 103.

FIG. 24 is a view when the state where the treatment tool 1 for an endoscope is attached to the endoscope apparatus 100 is viewed from a viewpoint of an operator of the endoscope apparatus 100.

As shown in FIG. 24, after the target portion to be treated is observed, the hook 46 is attached to the holding portion 102 of the endoscope apparatus 100 in a state where the treatment tool attachment-assisting instrument 90 is fixed to the forceps plug 103. In addition, the sheath 3 of the treatment tool 1 for an endoscope according to the present embodiment is inserted into the treatment tool channel 104 (refer to FIG. 1) of the endoscope apparatus 100 via the treatment tool attachment-assisting instrument 90. The operation portion 40 of the treatment tool 1 for an endoscope is connected to the endoscope apparatus 100 via the hook 46. Accordingly, for example, an operator of the treatment tool 1 for an endoscope can extract and input the sheath 3 with respect to forceps plug 103 of the endoscope apparatus 100 in a state of holding the endoscope apparatus 100 by the left hand and the sheath 3 by the right hand.

Figure 25:
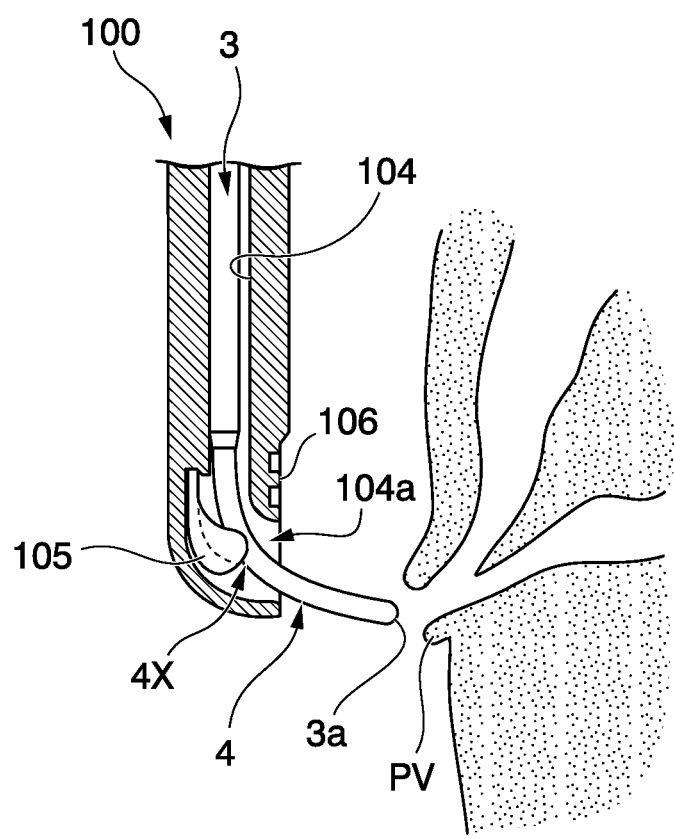
FIG. 25 is a view showing a use aspect of the treatment tool for an endoscope according to the first embodiment of the present invention.
Figure 26:
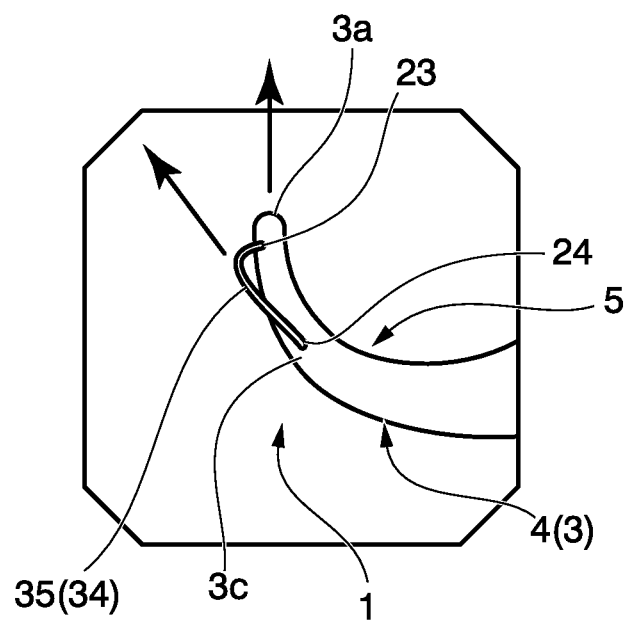
FIG. 26 is a schematic view showing the treatment tool for an endoscope which is reflected on an endoscopic image which is imaged using the endoscope apparatus according to the first embodiment of the present invention.

FIG. 25 is a view showing a process in which the treatment tool 1 for an endoscope is used. FIG. 26 is a schematic view showing the treatment tool 1 for an endoscope according to the present embodiment which is reflected on an endoscopic image which is imaged using the endoscope apparatus 100.

As shown in FIG. 25, the sheath 3 is operated by an operator, the distal end 3a of the sheath 3 protrudes from the distal end 104a (opening portion) of the treatment tool channel 104, and as shown in FIG. 26, imaging is performed by the imaging portion 106 of the endoscope apparatus 100.

In a procedure of the EST with respect to the duodenal papilla PV using the side view type endoscope apparatus 100, in a case where the image captured by the endoscope apparatus 100 is viewed from the viewpoint of a dial plate of a timepiece in which the upper center of the image is set to twelve o'clock, the direction of the imaging portion is adjusted such that the incision target portion of the duodenal papilla PV is reflected between eleven o'clock and twelve o'clock in the image captured by the endoscope apparatus 100. In this state, by incising the duodenal papilla PV such that the duodenal papilla PV is expanded from the opening portion of the duodenal papilla PV, a passage through which a calculus or the like in the duodenal papilla PV passes is formed.

First, an operator introduces a contrast agent into the duodenal papilla PV so as to examine traveling in a bile duct and a pancreatic duct and presence or absence of a calculus. That is, in order to perform the ERCP, the pre-curved portion 4 on the distal end 3a of the sheath 3 protrudes from the distal end 104a of the treatment tool channel 104 of the endoscope apparatus 100. Since the pre-curved portion 4 is curved in advance, the pre-curved portion 4 rotates with the center axis L1 of the sheath 3 as a rotation center until the pre-curved portion 4 follows the curved shape in the bending mechanism 107 or the raising stand 105 in the treatment tool channel 104.

In a process in which the distal portion of the pre-curved portion 4 passes through the raising stand 105, the pre-curved portion 4 rotates with the center axis L1 of the sheath 3 as a rotation center until the bending direction of the pre-curved portion 4 and the bending direction of the raising stand 105 coincide with each other. Subsequently, the distal end portion (drawing portion 5) of the pre-curved portion 4 enters an imaging visual field of the imaging portion 106 of the endoscope apparatus 100. An operator moves the proximal end 3b of the sheath 3 in the center axis L1 direction of the sheath 3 forward and backward in the operation portion 40 to adjust the position of the distal end portion (drawing portion 5) of the pre-curved portion 4. Specifically, the operator adjusts the position of the distal end portion of the pre-curved portion 4 to insert the distal end 3a of the sheath 3 into the duodenal papilla PV by moving the proximal end 3b of the sheath 3 forward and backward. In addition, even if the proximal end 3b of the sheath 3 is not positively rotated with the center axis L1 of the sheath 3 as the rotation center, since the pre-curved portion 4 is passively rotated according to the bending state of the bending mechanism 107 or the raising stand 105 of the endoscope apparatus 100, the distal end 3a of the sheath 3 is curved in the twelve o'clock direction in the endoscopic image.

As shown in FIG. 25, in the state where the distal end portion of the pre-curved portion 4 enters the imaging visual field of the imaging portion 106, the outer circumferential surface of the proximal end portion of the pre-curved portion 4 is pressed by the raising stand 105. The position of a pressed surface 4X (refer to FIG. 3B) which is pressed by the raising stand 105 on the outer circumferential surface of the pre-curved portion 4 is different from the positions at which the first distal communication hole 23 and the second distal communication hole 24 are formed on the outer circumferential surface of the pre-curved portion 4.

In a case where the determination of the position at which the distal end 3a of the sheath 3 is inserted into the duodenal papilla PV is difficult, the operator may insert the guide wire 80 from the first port 49 of the operation portion 40 into the first lumen 7 so as to allow the distal end 80a of the guide wire 80 to protrude from the distal end 7a of the first lumen 7. In this case, first, after the operator inserts the distal end 80a of the guide wire 80 into the duodenal papilla PV, subsequently, the operator can insert the distal end 3a of the sheath 3 into the duodenal papilla PV along the guide wire 80.

As shown in FIG. 26, when the distal portion of the sheath 3 is displayed on the endoscopic image by the imaging portion 106 and the bending direction of the pre-curved portion 4 on the endoscopic image is set to twelve o'clock, the curved knife portion 35 of the knife wire 30 protrudes from the first distal communication hole 23 and the second distal communication hole 24 in the direction closer to the eleven o'clock direction relative to the twelve o'clock direction. The operator inserts the sheath 3 from the forceps plug 103 into the treatment tool channel 104 while confirming the curved knife portion 35 being directed in the direction between eleven o'clock and twelve o'clock on the endoscopic image. Accordingly, the distal portion of the sheath 3 is extruded from the raising stand 105 of the endoscope apparatus 100, and the distal end 3a of the sheath 3 reaches the opening of the duodenal papilla PV and is inserted into the duodenal papilla PV.

If the sheath 3 is introduced into the duodenal papilla PV, the operator injects a contrast agent from the second port 62 so as to introduce the contrast agent into the bile duct or the pancreatic duct through the duodenal papilla PV from the distal discharge port 17 of the second lumen 15 of the sheath 3. According to the introduction of the contrast agent, the operator can easily recognize traveling in the bile duct and the pancreatic duct, presence or absence and the size of a calculus, or the like.

After the contrast agent is introduced, in a case where removal of the calculus is required, the EST is performed.

Figure 27:
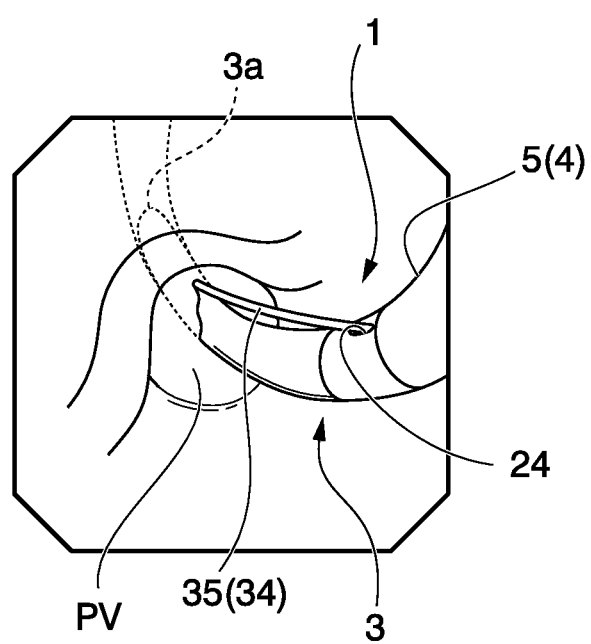
FIG. 27 is a schematic view showing an endoscopic image in a process of treatment using the treatment tool for an endoscope according to the first embodiment of the present invention.

FIG. 27 is a schematic view showing the endoscopic image in a process of treatment using the treatment tool 1 for an endoscope.

As shown in FIG. 27, after the sheath 3 is introduced into the duodenal papilla PV, in a state where the distal end portion (drawing portion 5) of the pre-curved portion 4 is disposed in the duodenal papilla PV by a predetermined length, the slider portion 71 of the operation portion 40 moves to the direction of the proximal end 68b of the shaft portion 68 in the direction of the center axis L6 of the rod-shaped portion 69 of the shaft portion 68, that is, the direction of the center axis L5 (refer to FIG. 2) of the handle-fixing portion 64. Accordingly, the capacity transmission portion 33 of the knife wire 30 moves in the direction of the proximal end 30b of the knife wire 30, and the distal end 30a of the knife wire 30 generates force which moves the portion of the first distal communication hole 23 of the sheath 3 in the proximal direction. Therefore, the proximal portion of the distal end 3a of the sheath 3 is deformed to be curved between the first distal communication hole 23 and the second distal communication hole 24. In addition, the incision portion 34 of the knife wire 30 is suspended in an arch shape with respect to the sheath 3.

The curved knife portion 35 (refer to FIG. 11) is positioned at the second quadrant Q2 in the above-described virtual coordinate system. Accordingly, when the bending direction of the pre-curved portion 4 which is imaged as the endoscopic image by the imaging portion 106 is set to twelve o'clock, the curved knife portion 35 comes into contact with the inner surface of the opening portion of the duodenal papilla PV at the position which is biased so as to be closer to the eleven o'clock direction relative to the twelve o'clock direction.

In the process in which the curved knife portion 35 is suspended in an arch shape with respect to the sheath 3, the operator supplies a high-frequency current from a high-frequency power supply device to the knife wire 30 through the connector 73 of the operation portion 40. Accordingly, the tissues which come into contact with the curved knife portion 35 are incised by the high-frequency current. The curved knife portion 35 is curved in a natural state where external force is not applied to the curved knife portion 35. Since the capacity transmission portion 33 of the knife wire 30 is moved in the direction of the proximal end 68b of the shaft portion 68 by the slider portion 71, the curved knife portion 35 is gradually deformed from the curved shape in the natural state into a straight-line shape. Specifically, the curved knife portion 35 is gradually deformed from the curved shape in the natural state into the straight-line shape along the straight-line direction in which the first distal communication hole 23 and the second distal communication hole 24 are connected to each other. If the curvature radius of the pre-curved portion 4 is set to be large, the knife wire 30 is gradually deformed from a straight-line shape into a curved shape. In this way, the curved state of the curved knife portion 35 is changed by the movement of the knife wire 30 which uses the slider portion 71.

Since the position of the duodenal papilla PV avoiding a main blood vessel is set so as to be reflected from eleven o'clock on the endoscopic image and the duodenal papilla PV is incised by the curved knife portion 35 at the position of eleven o'clock, it is possible to perform incision in a state where the amount of bleeding due to the incision of the duodenal papilla PV decreases.

After the incision with respect to the duodenal papilla PV ends, if necessary, the operator connects a syringe which is filled with the contrast agent to the second port 62 and injects the contrast agent from the second port 62 into the duodenal papilla PV through the second lumen 15. The path to the calculus which is the removal target is recognized on an X-line image by the contrast agent injected into the duodenal papilla PV.

Figure 28:
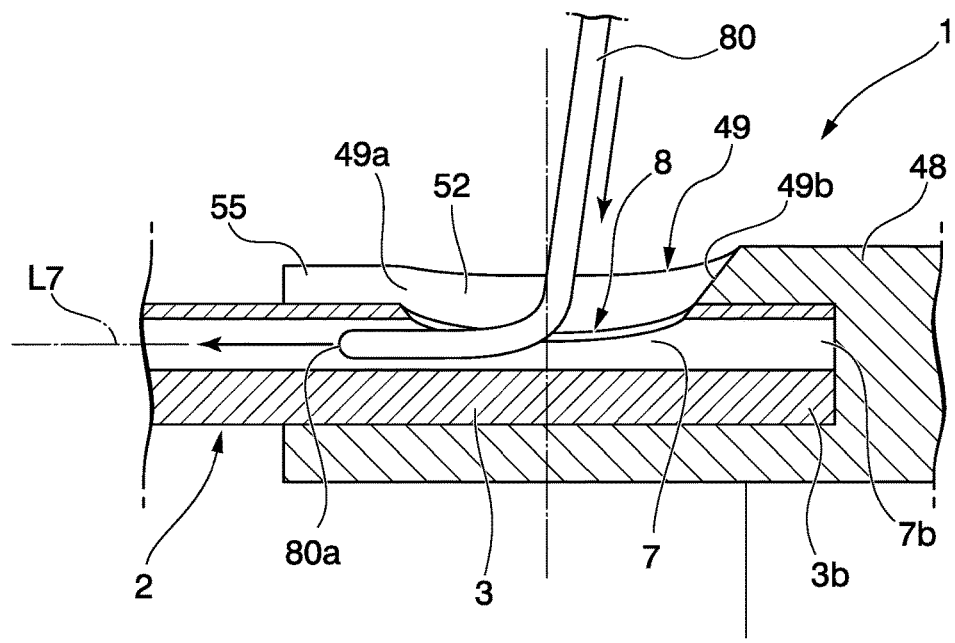
FIG. 28 is a view showing an aspect in which a guide wire is attached to the treatment tool for an endoscope according to the first embodiment of the present invention, and is a sectional view when viewed from line VIII-VIII shown in FIG. 6.
Figure 29:
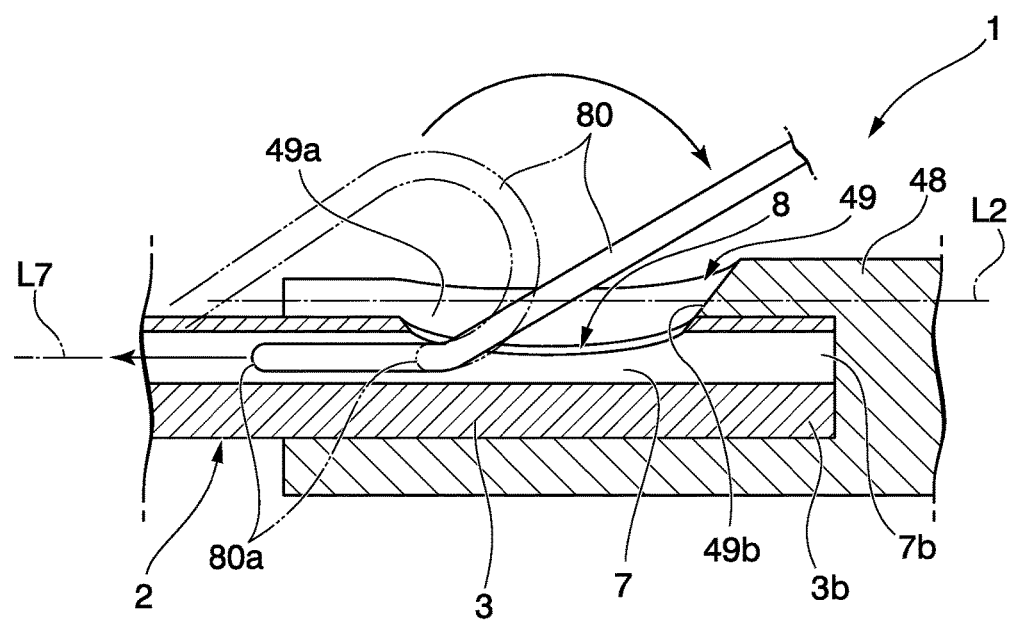
FIG. 29 is a view showing another example in which the guide wire is attached to the treatment tool for an endoscope according to the first embodiment of the present invention, and is a sectional view when viewed from line VIII-VIII shown in FIG. 6.

FIG. 28 is a view showing an example in which the guide wire 80 is attached to the treatment tool 1 for an endoscope, and is a partial sectional view when viewed from line VIII-VIII shown in FIG. 6. FIG. 29 is a view showing another example in which the guide wire 80 is attached to the treatment tool 1 for an endoscope, and is a partial sectional view when viewed from line VIII-VIII shown in FIG. 6.

After an operator recognizes the traveling in a bile duct or a pancreatic duct by an X-ray image, the operator introduces the guide wire 80, which is inserted into the bile duct or the pancreatic duct, from the duodenal papilla PV. In the present embodiment, a case where the guide wire 80 is introduced into the bile duct according to the traveling in the bile duct is exemplified.

The angle type guide wire 80 having a bending structure on the distal end is used as the guide wire 80 inserted into the bile duct such that the guide wire 80 is selectively inserted into the bile duct in the branched portion between the bile duct and the pancreatic duct by an operator and the guide wire 80 is suitably guided in a desired direction in the branch inside the bile duct by the operator.

The angle type guide wire 80 has a distal end portion which has high flexibility and a bent shape so as to flexibly follow the inner wall of the bile duct and have a restoring force in a predetermined bending direction. When the angle type guide wire 80 is attached to the treatment tool 1 for an endoscope, an operator holds a region adjacent to the proximal portion of a portion which has a bent shape on the distal portion of the guide wire 80. Next, as shown in FIG. 28, the operator inserts the vicinity 801 of the distal end 80a of the guide wire 80 into the first lumen 7 from the first port 49. At this time, the operator inserts the guide wire 80 into the first port 49 in a state where the guide wire 80 is inclined such that the distal end 80a of the guide wire 80 faces the distal end 49a side in the first port 49.

A method of inserting the distal end 80a of the guide wire 80 into the first port 49 can be appropriately selected according to the curved shape of the proximal region on the distal end 80a of the angle type guide wire 80.

For example, in a case where the curved shape portion 811 of the proximal region on the distal end 80a of the guide wire 80 is bent so as to form an obtuse angle as the guide wire 80 shown in FIG. 16, as shown in FIG. 28, the operator inserts the guide wire 80 into the first port 49 such that a portion from the distal end 80a of the guide wire 80 to the bending portion is parallel with the center axis L7 of the first lumen 7. As a result, the guide wire 80 is smoothly inserted into the first lumen 7.

In a case where the curved shape portion 812 of the proximal region on the distal end 80a of the guide wire 82 is bent so as to form a semi-arc shape as the guide wire 82 shown in FIG. 17A, the operator inserts the distal end 80a into the first port 49 such that the curved shape portion 812 of the guide wire 82 is hooked to the distal end 49a of the first port 49 (refer to FIG. 29). Thereafter, the operator bends the guide wire 80 in the proximal end 49b direction of the first port 49 so as to deform the guide wire 80 in a straight-line shape, and inserts the guide wire 80 into the first lumen 7. As a result, the guide wire 80 is smoothly inserted into the first lumen 7.

Even when the method of inserting the distal ends 80a of the guide wires 80 and 81 into the first port 49 is any of the above-described cases, the method is performed in a state where an operator views the inner surface 7c of the first lumen 7 through the first port 49. As a result, an operator can easily insert the distal end 80a of the guide wire 80 into the first lumen 7.

In the state where the operation portion 40 is connected to the holding portion 102 of the endoscope apparatus 100 by the hook 46, the opening of the first port 49 faces the proximal side of the endoscope apparatus 100. Accordingly, an operator can insert the distal end 80a of the guide wire 80 into the first lumen 7 in a state of viewing the first lumen 7 of the sheath 3 through the first port 49.

In addition, the first port 49 includes a long-hole shaped opening which is long in a longitudinal axis L2 direction extending in the straight-line direction in which the distal end 48a of the connection portion 48 to the sheath 3 and the proximal end 48b of the connection portion 48 to the sheath 3 are connected to each other. Accordingly, the guide wire 80 inserted into the first port 49 can be operated so as to move forward and backward in the direction (direction which is slightly inclined with the center axis L7 of the first lumen 7) along the approximately center axis L7 of the first lumen 7. Therefore, the operator operates the guide wire 80 so as to easily move the guide wire 80 forward and backward by the right hand, and it is possible to prevent the occurrence of buckling of the guide wire 80.

That is, according to the treatment tool 1 for an endoscope of the present embodiment, from the state where the operator holds the endoscope apparatus 100 by the left hand and moves the sheath 3 forward and backward by the right hand, the operator switches the holding target of the right hand from the sheath 3 to the guide wire 80 and can easily insert the guide wire 80 into the first port 49 or move the guide wire 80 forward and backward by the right hand.

In a case where the operator inserts the guide wire 80 into the first lumen 7 before the operator inserts the distal end 3a of the sheath 3 into the duodenal papilla PV, the operator may use the guide wire 80 which has already been inserted, or may replace the inserted guide wire with the above-described angle type guide wire 80.

The operator causes the guide wire 80 to protrude from the distal end 3*a* of the sheath 3, and guides the guide wire 80 to a desired position in the bile duct. At this time, if necessary, the operator may rotate the guide wire 80 around the center axis so as to move the guide wire 80 such that the distal end 80*a* of the guide wire 80 is inserted into a desired branch in a branching portion of the bile duct.

Figure 30:
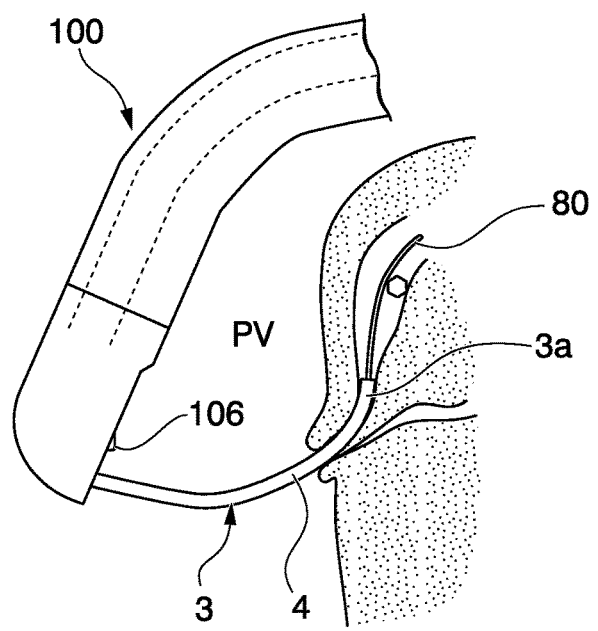
FIG. 30 is a view showing a process when the treatment tool for an endoscope according to the first embodiment of the present invention is used.

FIG. 30 is a view showing a process when the treatment tool 1 for an endoscope is used. As shown in FIG. 30, for example, the guide wire 80 is inserted until the distal end 80*a* of the guide wire 80 is positioned at the position advancing toward the inner side to a certain extent beyond the calculus to be removed from the inner portion of the bile duct.

Figure 31:
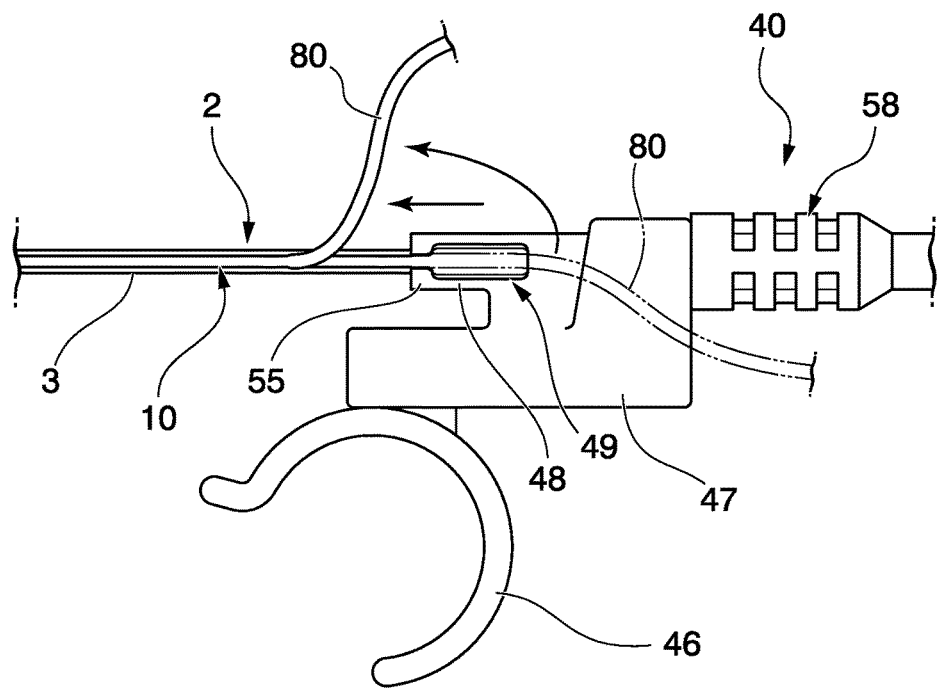
FIG. 31 is a view showing a process in which the treatment tool for an endoscope is removed from the endoscope apparatus in a state where the guide wire which is attached to the treatment tool for an endoscope according to the first embodiment of the present invention remains.
Figure 32:
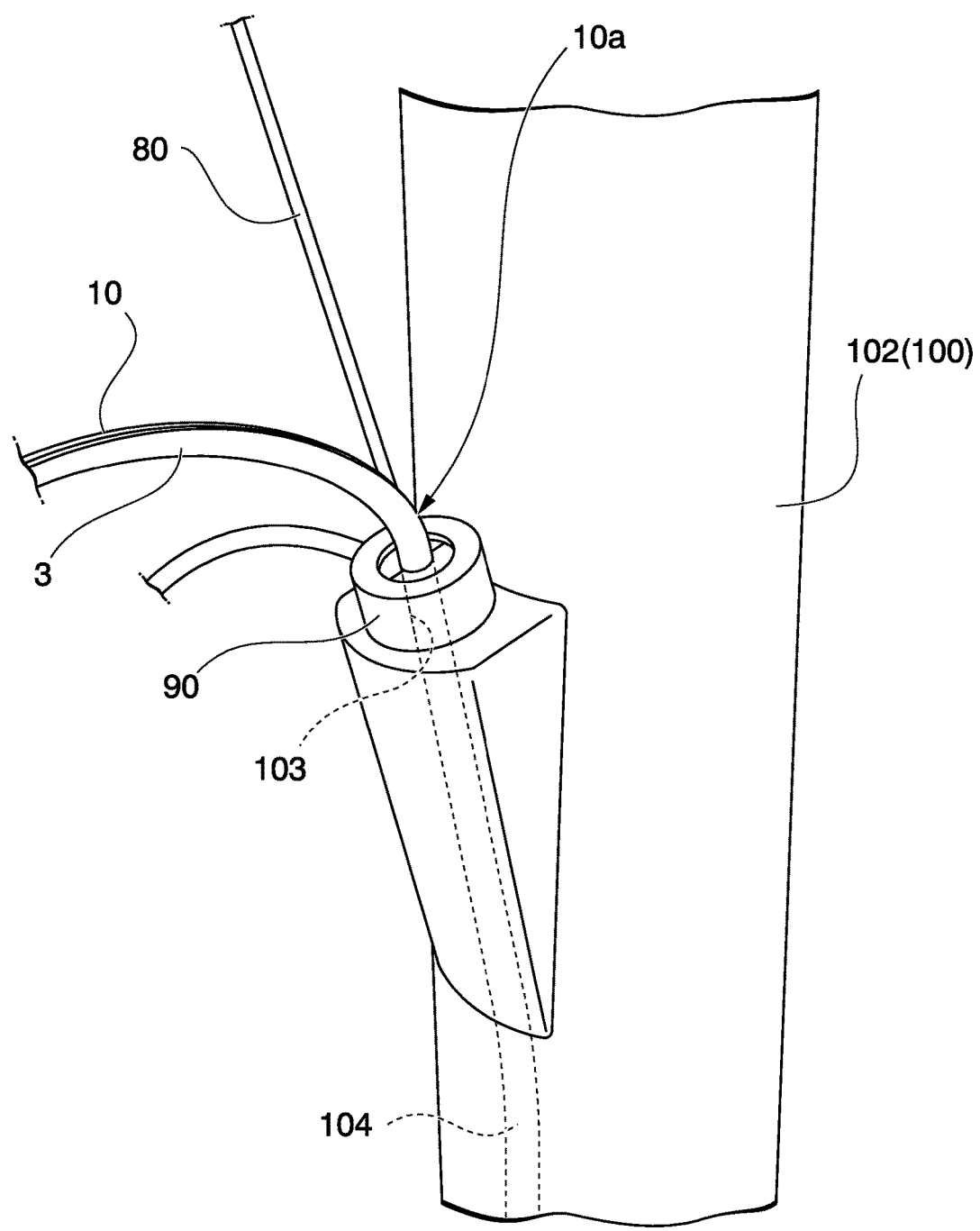
FIG. 32 is a view showing a process in which the sheath and the guide wire of the treatment tool for an endoscope according to the first embodiment of the present invention are separated from each other.
Figure 33:
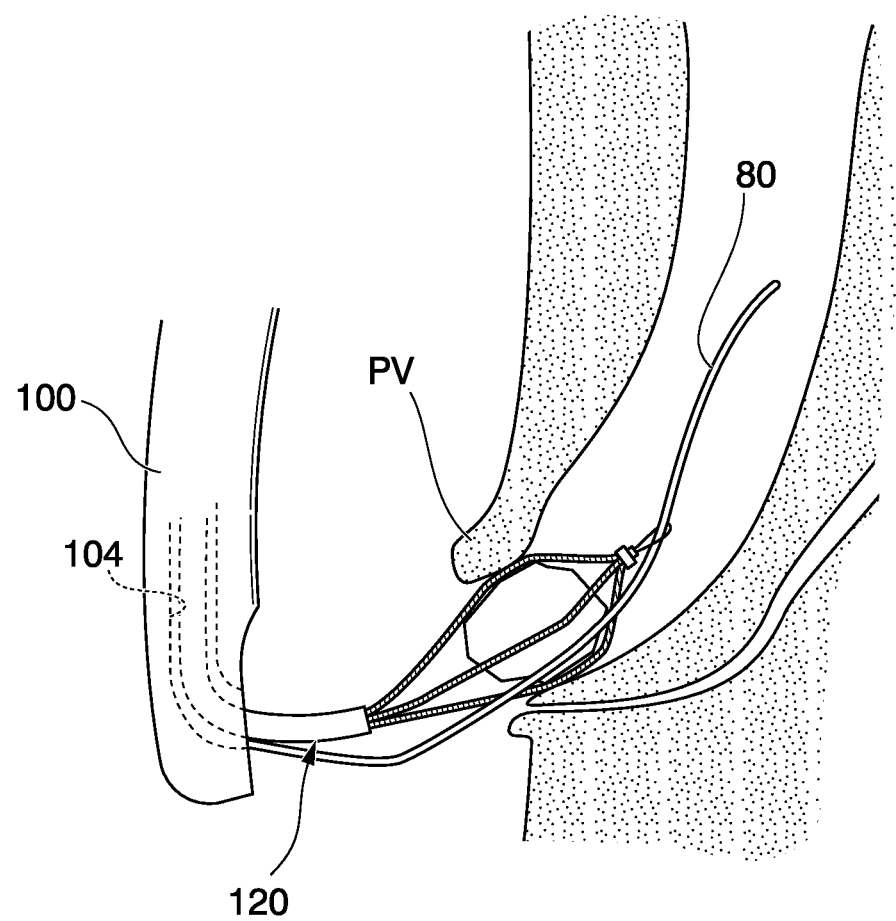
FIG. 33 is a view showing an example of treatment which is performed after the removal of the treatment tool for an endoscope according to the first embodiment of the present invention.

FIG. 31 is a view showing a process in which the treatment tool 1 for an endoscope is removed from the endoscope apparatus 100 in a state where the guide wire 80 which is attached to the treatment tool 1 for an endoscope remains. FIG. 32 is a view showing a process in which the sheath 3 and the guide wire 80 of the treatment tool 1 for an endoscope are separated from each other. FIG. 33 is a view showing an example of treatment which is performed after the removal of the treatment tool 1 for an endoscope.

After the guide wire 80 reaches a predetermined position, the treatment tool 1 for an endoscope is removed in the state where the guide wire 80 remains in the body. This is performed in order to introduce the known endoscope calculus removal instrument (basket forceps, balloon, or the like) for removing the calculus into the bile duct instead of the treatment tool 1 for an endoscope according to the present embodiment.

As shown in FIG. 31, in order to remove the treatment tool 1 for an endoscope, first, the operator detaches the guide wire 80 from the first port 49, which is disposed in the distal configuration portion 41 of the operation portion 40, through the notch portion 55. At this time, the operator moves the guide wire 80 with respect to first port 49 from the proximal end 55*b* of the notch portion 55 of the first port 49 to the distal end 55*a* of the notch portion 55 through the inner portion of the notch portion 55 without changing the position of the distal end 80*a* of the guide wire 80. In the process in which the guide wire 80 passes through the notch portion 55 of the first port 49, the guide wire 80 is gradually extracted from the guide wire accommodation portion 9 to the outside of the sheath 3 through the slit portion 10.

Subsequently, as shown in FIG. 32, the operator moves the sheath 3 in the direction of the proximal end of the treatment tool channel 104 while supporting the guide wire 80 such that the position of the guide wire 80 is not changed. In the process in which the operator moves the sheath 3 in the direction of the proximal end of the treatment tool channel 104, the sheath 3 is gradually detached from the guide wire 80.

If the outlet portion 12 (refer to FIG. 10) of the first lumen 7 in the sheath 3 reaches the position of the forceps plug 103, the operator moves the sheath 3 in the direction of the proximal end 80*b* of the guide wire 80 while supporting the guide wire 80 against the force which is generated by the guide wire 80 to be moved in the direction of the proximal end 80*b*. The operator extracts the outlet portion 12 of the sheath 3 from the forceps plug 103 without changing the position of the guide wire 80 in the body. Thereafter, the operator moves the distal portion of the sheath 3, in which the outlet portion 12 of the sheath 3 is disposed, in the direction of the proximal end 80*b* of the guide wire 80, and detaches the sheath 3 from the guide wire 80.

If the sheath 3 is detached from the guide wire 80, the operator attaches the known endoscope calculus removal instrument (for example, basket forceps 120 shown in FIG. 33) to the guide wire 80, and guides the endoscope calculus removal instrument to the calculus which is the removal target through the treatment tool channel 104 of the endoscope apparatus 100.

Next, an example will be described, in which an operator who operates the endoscope apparatus 100 and an operator who operates the treatment tool 1 for an endoscope are different from each other.

In this example, the operator who operates the treatment tool 1 for an endoscope holds the operation portion 40 of the treatment tool 1 for an endoscope by one hand, and can insert the guide wire 80 into the first port 49 and adjust the position of the guide wire 80 by the other hand. The operator of the endoscope apparatus 100 and the operator of the treatment tool 1 for an endoscope cooperate with each other with respect to mutual operations, and thus, it is possible to perform the same treatment as that of the above example in which one operator operates the endoscope apparatus 100 and the treatment tool 1 for an endoscope.

As described above, in the treatment tool 1 for an endoscope according to the present embodiment, since the first port 49 is disposed in the direction in which the inner surface 7*c* of the first lumen 7 is viewed through the opening of the first port 49 when the hook 46 is attached to the holding portion 102 of the endoscope apparatus 100, it is possible to easily insert the guide wire 80 into the first port 49 in a case where the hook 46 is attached to the holding portion 102 of the endoscope apparatus 100 and one person uses the endoscope apparatus 100 and the treatment tool 1 for an endoscope.

In addition, in the treatment tool 1 for an endoscope according to the present embodiment, since the first port 49 is disposed in the above-described direction, one operator can easily perform the forward and backward movements and the rotating operation of the guide wire 80 when the guide wire 80 is inserted from the first port 49 into the first lumen 7 with the holding portion 102 of the endoscope apparatus 100.

The treatment tool 1 for an endoscope is configured such that the inlet portion 8 of the first lumen 7 can be viewed when the first port 49 has an elliptical opening shape and the guide wire 80 is inserted into the first port 49. Accordingly, even when the angle type guide wire 80 in which the distal end is bent, is adopted, it is possible to easily introduce the distal end into the first lumen 7.

The first port 49 has an elliptical opening shape. Accordingly, since the guide wire 80 smoothly moves forward and backward in the direction approximately along the center axis L7 of the first lumen 7 after the guide wire 80 is inserted into the first port 49, it is possible to smoothly move the guide wire 80 forward and backward.

In the treatment tool 1 for an endoscope according to the present embodiment, when the guide wire 80 is inserted into the first port 49, the positional relationship between the handle-fixing portion 64 and the first port 49 is set such that the guide wire 80 protruding from the first port 49 does not interfere with the handle portion 67. Accordingly, it is possible to easily operate the handle portion 67 in a state where the guide wire 80 is attached to the treatment tool 1 for an endoscope.

In the treatment tool 1 for an endoscope according to the present embodiment, the finger-hooking portion 74 of the slider portion 71 is provided on the inner surface orthogonal to the center axis L3 of the opening of the first port 49. Accordingly, the finger-hooking portion 74 does not easily interfere with the guide wire 80, and it is possible to easily move the slider portion 71 using the finger-hooking portion 74. That is, since the slider portion 71 is not disposed in the direction in which the guide wire 80 is inserted into and extracted from the first port 49, the operation of the slider portion 71 and the operation of the guide wire 80 do not interfere with each other.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A treatment tool for an endoscope which is inserted into a treatment tool channel of an endoscope apparatus which includes a tubular member that is capable of being operated to be bent and a bending operation section that is provided to bend the tubular member, comprising:
    a sheath which includes a proximal region, a distal region, an outer circumference surface, and an inner circumference surface, the inner circumference surface being formed to define a lumen which is extended along a longitudinal axis of the sheath and through which a guide wire is inserted;
    a slit portion which extends from the proximal region to the distal region in the longitudinal axis direction of the sheath and is formed to extend through the sheath from the inner circumference surface to the outer circumference surface;
    an inlet portion which includes an opening that is formed at the outer circumference surface in the proximal region of the sheath, the opening being formed to communicate with the slit portion, and being formed to extend through the sheath from the inner circumference surface to the outer circumference surface in a same direction with that of the slit portion,
    a locking portion which is connected to the sheath and which is configured to lock to the endoscope, and
    an operation portion including:
        a tubular portion which includes an inner space into which the proximal region of the sheath is inserted, and a communication port communicating with the inner space;
        a port-fixing portion provided to fix the proximal region of the sheath to the tubular portion such that a direction of the opening of the inlet portion coincides with a direction of the communication port of the tubular portion; and
        a notch portion configured to communicate with the slit portion from a distal end of the communication port of the tubular portion to a distal end of the tubular portion along a longitudinal axis of the slit portion.

2. The treatment tool for an endoscope according to claim 1, further comprising:
    an insertion portion which includes the sheath, wherein the operation portion is disposed at a proximal end of the insertion portion,
    the communication port includes a through-hole formed to communicate with the inlet portion and configured to receive the guide wire therethrough, and
    the through-hole is open to a direction intersecting a center axis of the lumen.

3. The treatment tool for an endoscope according to claim 2,
    wherein the locking portion includes a hook which has elasticity, the hook being formed in a C-shape so as to surround a portion of an outer circumferential surface of a holding portion of the endoscope apparatus, and
    wherein a center axis of the through-hole of the communication port and a center axis of a circumference on an inner circumferential surface surrounding the holding portion in the hook are parallel with each other.

4. The treatment tool for an endoscope according to claim 3, wherein
    the sheath includes the slit portion which extends in the center axis direction of the sheath and causes communication between the inside of the lumen and the outside of the sheath,
    wherein the notch portion is C-shaped, and
    the operation portion includes,
        a connection portion in which the communication port is formed and which is connected to the proximal end of the sheath,
        an extension portion which is connected to the hook, and
        a main body portion which is connected to both of the connection portion and the extension portion such that the hook and the notch portion are spaced from each other.

5. The treatment tool for an endoscope according to claim 2,
    wherein the slit portion is formed between the inlet portion and an outlet portion of the treatment tool, and is formed such that an opening width in the circumferential direction of the sheath is smaller than the inner diameter of the lumen, and
    wherein the sheath is fixed to the operation portion such that an opening edge portion of the inlet portion approximately coincides with an inner opening edge portion forming a contour on the inner circumferential side of the communication port or is positioned inside the inner opening edge portion forming the contour on the inner circumferential side of the communication port, when the opening edge portion of the inlet portion and the inner opening edge portion forming the contour on the inner circumferential side of the communication port are projected in an extension direction of a straight line which connects the center axis of the lumen and the center axis of the sheath.

6. The treatment tool for an endoscope according to claim 1, further comprising:
    a knife wire which is disposed on the distal region of the sheath and provided to incise tissues,
    wherein the notch portion has a C-shape in a cross section perpendicular to the longitudinal axis of the sheath.

7. The treatment tool for an endoscope according to claim 1, further comprising:
    an insertion portion which includes the sheath, wherein the operation portion is disposed at a proximal end of the insertion portion,
    the insertion portion includes,
        a knife wire which is disposed at the sheath to incise tissues of the body,
        a second lumen which is formed in the sheath, and includes a space configured to receive flowing liquid, an injection port at the distal region of the sheath, and a connection port at the proximal region of the sheath, and a third lumen which is formed in the sheath, into which the knife wire is inserted, and which includes a horizontal hole portion, through which the knife wire is exposed, at the distal region of the sheath, and an opening at the proximal region of the sheath, the operation portion includes, a first port which communicates with the inlet portion, and at which a through-hole, into which the guide wire is insertable, is formed, a second port which communicates with the second lumen, and a handle portion at which a slider portion for interlocking with the knife wire is formed, the first port is a hole which has a major axis in a center axis direction of the lumen, and the slider portion includes a finger-hooking portion which protrudes in a direction of a plane orthogonal to a center axis of the through-hole of the first port.

8. The treatment tool for an endoscope according to claim 7, wherein the operation portion includes a shaft portion which has a center axis in a direction inclined to the longitudinal axis of the sheath and is connected to the slider portion such that the slider portion is movable forward and backward in the direction of the center axis.

9. The treatment tool for an endoscope according to claim 1, wherein the locking portion is configured to be locked to the endoscope apparatus, in a state in which an opening direction of the inlet portion of the sheath faces the bending operation section.

10. The treatment tool for an endoscope according to claim 1, wherein the locking portion is connected to the sheath via the operation portion.

11. The treatment tool for an endoscope according to claim 1, wherein the port-fixing portion is provided to fix the proximal region of the sheath to the tubular portion such that the direction of the opening of the inlet portion coincides with the direction of the communication port of the tubular portion, in a state in which the sheath is inserted into the treatment tool channel and the locking portion is locked to the endoscope apparatus.

* * * * *